(12) United States Patent
Kucera et al.

(10) Patent No.: US 8,193,342 B2
(45) Date of Patent: Jun. 5, 2012

(54) METHOD FOR PREPARING FURANOSE COMPOUNDS

(75) Inventors: David Kucera, Del Mar, CA (US); Gregory J. Haley, San Diego, CA (US); Erik J. Rueden, Belmont, CA (US); Tingmin Wang, San Diego, CA (US)

(73) Assignee: Anadys Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 13/069,426

(22) Filed: Mar. 23, 2011

(65) Prior Publication Data

US 2011/0172447 A1 Jul. 14, 2011

Related U.S. Application Data

(62) Division of application No. 11/873,202, filed on Oct. 16, 2007, now Pat. No. 7,928,085.

(60) Provisional application No. 60/852,002, filed on Oct. 17, 2006, provisional application No. 60/899,405, filed on Feb. 5, 2007, provisional application No. 60/953,597, filed on Aug. 2, 2007.

(51) Int. Cl.
*C07H 1/08* (2006.01)
(52) U.S. Cl. ...................................... 536/124
(58) Field of Classification Search .................. 536/124
See application file for complete search history.

(56) References Cited

U.S. PATENT DOCUMENTS

| 5,532,374 | A | 7/1996 | Lee et al. |
| 7,560,544 | B2 | 7/2009 | Webber et al. |
| 2003/0144512 | A1 | 7/2003 | Ikemoto et al. |
| 2006/0160830 | A1 | 7/2006 | Webber et al. |
| 2006/0229322 | A1 | 10/2006 | Cid |

FOREIGN PATENT DOCUMENTS

WO WO 2007/150002 12/2007

OTHER PUBLICATIONS

Gruner et al. Design, synthesis, and NMR structure of linear and cylclis oligomers containing novel furanoid sugar amino acids. Chem. Eur. J., 2002, vol. 8(19), pp. 4365-4376, p. 4367.
Surzhykov et al. Novel 4-branched nucleosides, Nucleosides & Nucleotides, 1994, vol. 13(10), pp. 2283-2305, p. 2291, p. 2302, para 2.
Chiu et al. Nucleosides. LXXXIV. Total Synthesis of Pantopyranin C, a Nucleosides Elaborated by Streptomyces griseochromogenes. Journal of Organic Chemistry, 1973, vol. 38(20), pp. 3622-3624, p. 3623, para. 2.
International Preliminary Report on Patentability for International Application No. PCT/US2007/081526, dated Apr. 22, 2009.
Valdivia, V. et al., "Toward a novel series of furanopyrimidine nucleoside analogues," Tetrahedron Letters, vol. 46, No. 38, pp. 6511-6514 (Sep. 19, 2005).
Brandstetter, T. et al., "Synthesis and oxidative activation of an oxabicyclo[7.2.1]enediyne," Tetrahedron, vol. 50, No. 5, pp. 1435-1448 (Jan. 31, 1994).

*Primary Examiner* — Elli Peselev
(74) *Attorney, Agent, or Firm* — Connolly Bove Lodge & Hutz LLP; Mark J. Pino

(57) ABSTRACT

The present disclosure relates to methods for preparing furanose compounds of Formula (3), which are useful as intermediates in the preparation of a p-toluene sulfonic acid salt of 5-amino-3-(2'-O-acetyl-3'-deoxy-beta-D-ribofuranosyl)-3H-thiazolo[4,5-d]pyrimidin-2-one and the like.

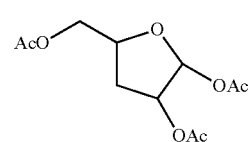

Formula (3)

10 Claims, 2 Drawing Sheets

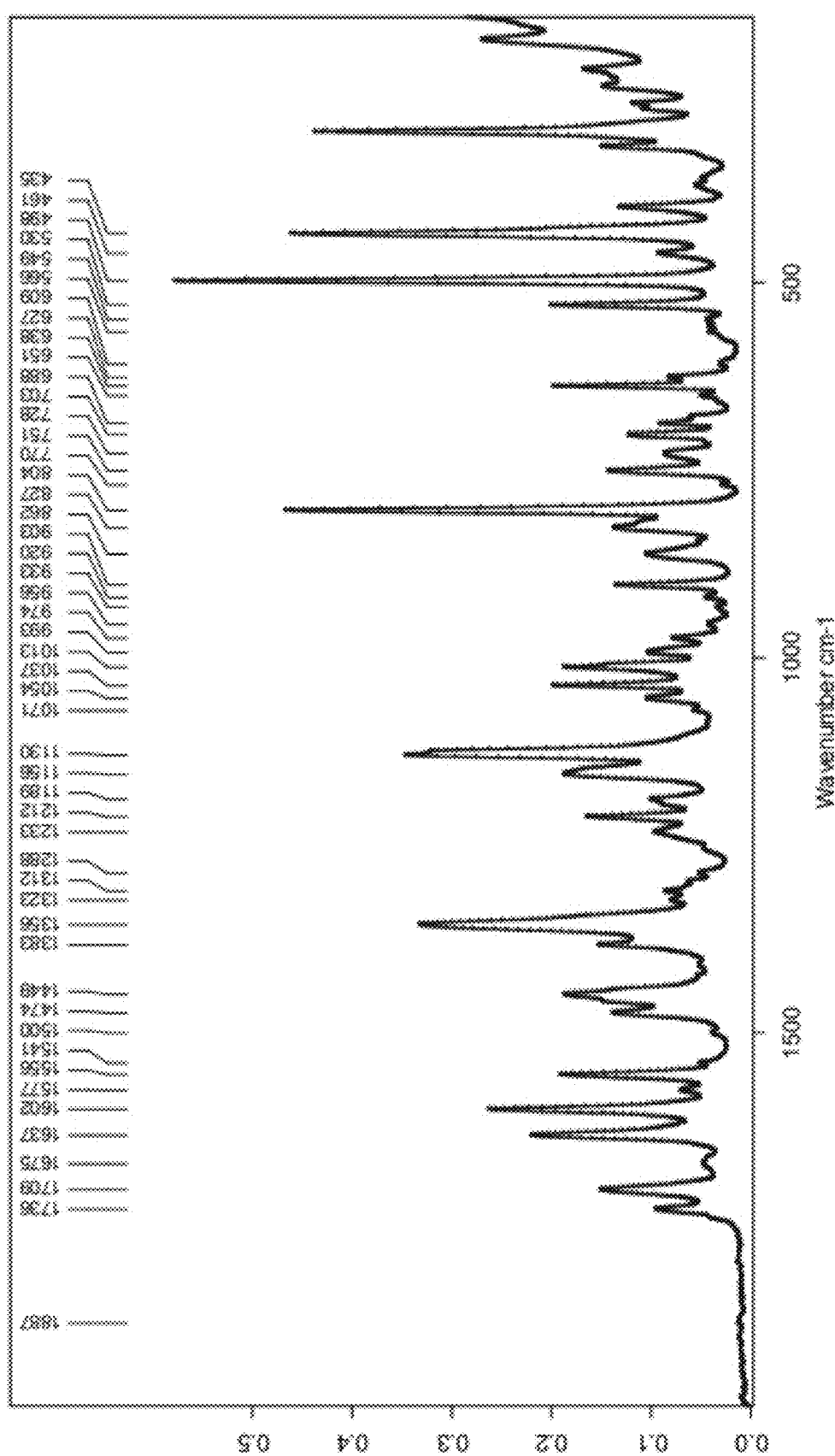
Fig. 1: FT-Raman spectrum of Formula (1)

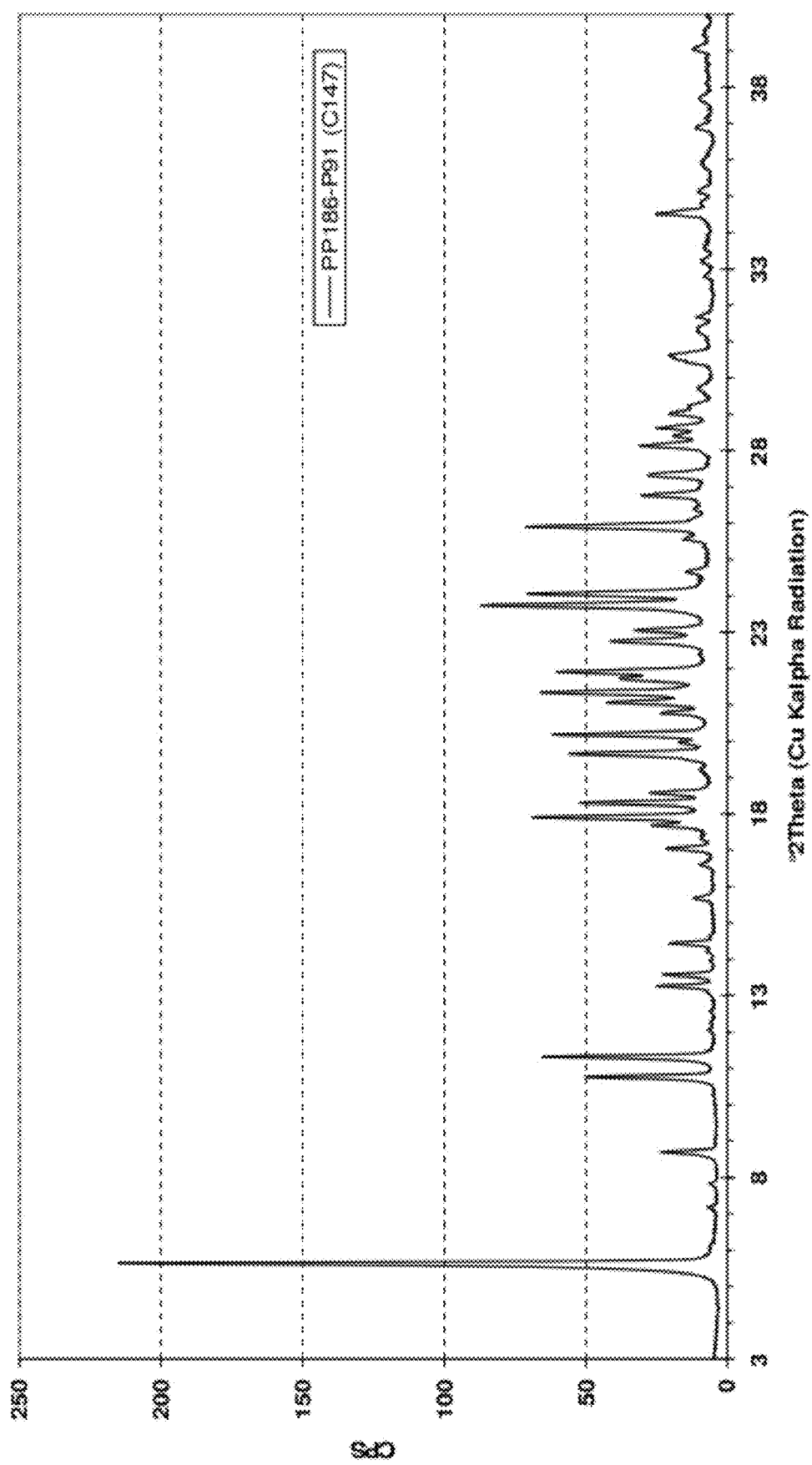
Fig. 2: PXRD pattern of Formula (1)

METHOD FOR PREPARING FURANOSE COMPOUNDS

RELATED APPLICATIONS

This application is a divisional of U.S. application Ser. No. 11/873,202 filed Oct. 16, 2007 (now patented as U.S. Pat. No. 7,928,085) which claims the benefit of U.S. Provisional Patent Application Nos. 60/852,002 filed Oct. 17, 2006; U.S. Provisional Patent Application No. 60/899,405 filed Feb. 5, 2007; and U.S. Provisional Patent Application No. 60/953,597 filed Aug. 2, 2007, which are incorporated herein by reference in their entireties.

FIELD OF THE DISCLOSURE

The present disclosure relates to p-toluene sulfonic acid salt of 5-amino-3-(2'-O-acetyl-3'-deoxy-beta-D-ribofuranosyl)-3H-thiazolo[4,5-d]pyrimidin-2-one and to its use in treating conditions such as viral infections, tumors, and cancer. Also disclosed is a method for preparing the p-toluene sulfonic acid salt of 5-amino-3-(2'-O-acetyl-3'-deoxy-β-D-ribofuranosyl)-3H-thiazolo[4,5-d]pyrimidin-2-one and methods for producing furanose compounds which are useful intermediates in the preparation of pharmaceutical compounds such as p-toluene sulfonic acid salt of 5-amino-3-(2'-O-acetyl-3'-deoxy-β-D-ribofuranosyl)-3H-thiazolo[4,5-d]pyrimidin-2-one and the like.

BACKGROUND OF THE DISCLOSURE

Nucleoside analogs are an important class of compounds that are useful in the treatment of disease. For example, nucleoside analogs have been used in the treatment of cancers and viral infections. After entry into a cell, nucleoside analogs are frequently phosphorylated by nucleoside salvage pathways in which the analogs are phosphorylated to the corresponding mono-, di-, and triphosphates. Among other intracellular destinations, triphosphorylated nucleoside analogs often serve as substrates for DNA or RNA polymerases and become incorporated into DNA and/or RNA. Where triphosphorylated nucleoside analogs are strong polymerase inhibitors, they may induce premature termination of a nascent nucleic acid molecule. Where triphosphorylated nucleoside analogs are incorporated into nucleic acid replicates or transcripts, gene expression or disruption of function may result.

Some nucleoside analogs may be efficacious because of their ability to inhibit adenosine kinase. Adenosine kinase catalyzes the phosphorylation of adenosine to adenosine 5'-monophosphate (AMP). Inhibition of adenosine kinase may effectively increase the extracellular level of adenosine in humans and thereby serve as a treatment of ischemic conditions such as stroke, inflammation, arthritis, seizures, and epilepsy.

The last few decades have seen significant efforts expended in exploring therapeutic uses of nucleoside analogs. For example, certain pyrimido[4,5-d]pyrimidine nucleosides are disclosed in U.S. Pat. No. 5,041,542 to Robins et al. as being effective in treatment against L1210 in BDF1 mice. Additionally, 3-β-D-ribofuranosylthiazolo[4,5-d]pyrimidines demonstrating significant immunoactivity, including murine spleen cell proliferation and in vivo activity against Semliki Forest virus, are disclosed U.S. Pat. Nos. 5,041,426 and 4,880,784 to Robins et al. A number of publications have also described non-glycosyl derivatives of the thiazolo[4,5-d]pyrimidine moiety. See, e.g., U.S. Pat. Nos. 5,994,321 and 5,446,045; Revankar et al., J. HET. CHEM., 30, 1341-49 (1993); Lewis et al., J. J. HET. CHEM., 32, 547-56 (1995).

3,5-Disubstituted-3H-thiazolo[4,5-d]pyrimidin-2-one compounds have been shown to have immunomodulatory activity. The preparation and usefulness of this class of compounds is discussed in U.S. Application Publication No. US2006/0160830 (U.S. application Ser. No. 11/304,691), which is incorporated herein by reference in its entirety. This application describes the synthesis of the free base compound 5-amino-3-(2'-O-acetyl-3'-deoxy-beta-D-ribofuranosyl)-3H-thiazolo[4,5-d]pyrimidin-2-one. The purity of this compound may vary based on purification methods due to the amorphous nature of the free base. Adequate purification of the free base may be limited to the use of certain solvents which are not acceptable for human consumption. In addition, the amorphous form (free base) of this compound tends to be hydroscopic which may make the compound susceptible to hydrolysis. Accordingly, a method for producing a crystalline form of this compound with high purity and stability having low amounts of non-toxic solvent is desirable for pharmaceutical applications.

SUMMARY OF THE DISCLOSURE

The disclosure is directed to p-toluene sulfonic acid salt of 5-amino-3-(2'-O-acetyl-3'-deoxy-beta-D-ribofuranosyl)-3H-thiazolo[4,5-d]pyrimidin-2-one, shown below in Formula (1) and pharmaceutical compositions comprising the salt.

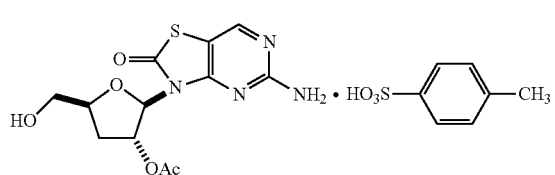

The compound of Formula 1 is used in methods for treating or preventing disease. For instance, a compound of Formula 1 is used in methods of treating or preventing the onset and/or progression of tumors or cancers. Also disclosed are methods of treating or preventing infection by a pathogen such as, for example, viruses including Hepatitis B virus or Hepatitis C virus. The compound of Formula 1 is also used in methods of modulating immune cytokine activity.

In another embodiment, the present disclosure is directed to a method for preparing p-toluene sulfonic acid salt of 5-amino-3-(2'-O-acetyl-3'-deoxy-β-D-ribofuranosyl)-3H-thiazolo[4,5-d]pyrimidin-2-one (1).

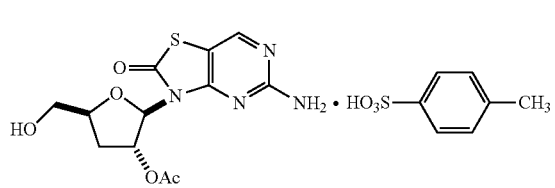

The method comprises the steps of:
(i) coupling 5-amino-3H-thiazolo[4,5-d]pyrimidin-2-one (2) with a deoxyribofuranose (3) to form a compound of Formula (4)

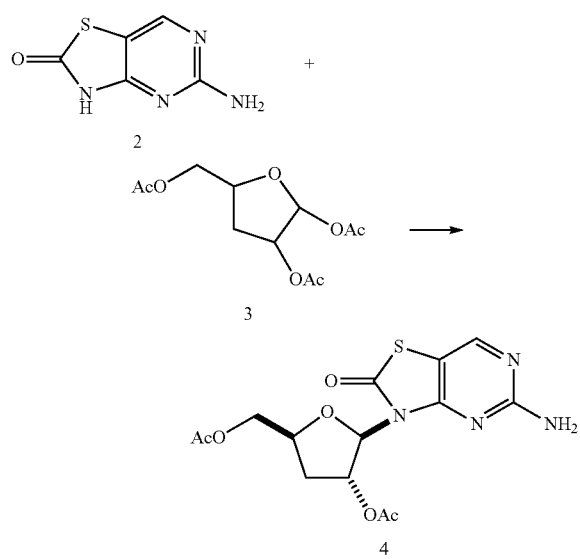

(ii) selectively cleaving the 5' acetate on the compound of Formula (4) to form 5-amino-3-(2'-O-acetyl-3'-deoxy-β-D-ribofuranosyl)-3H-thiazolo[4,5-d]pyrimidin-2-one (5)

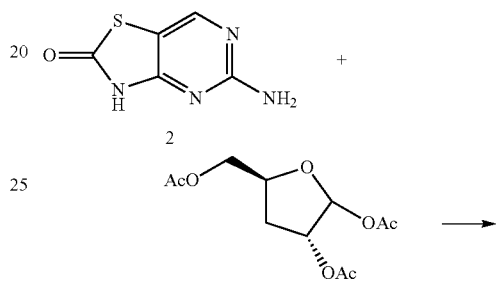

and (iii) reacting 5-amino-3-(2'-O-acetyl-3'-deoxy-β-D-ribofuranosyl)-3H-thiazolo[4,5-d]pyrimidin-2-one (5) with p-toluene sulfonic acid to form p-toluene sulfonic acid salt of 5-amino-3-(2'-O-acetyl-3'-deoxy-β-D-ribofuranosyl)-3H-thiazolo[4,5-d]pyrimidin-2-one (1)

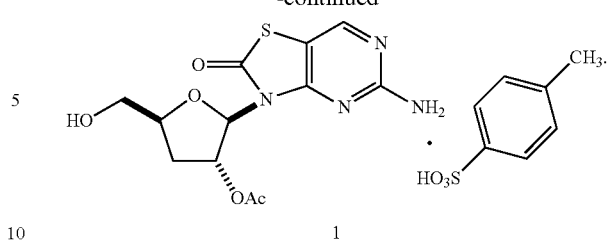

In another embodiment, step (i) comprises coupling 5-amino-3H-thiazolo[4,5-d]pyrimidin-2-one (2) with a deoxyribofuranose of Formula (3B) to form a compound of Formula (4)

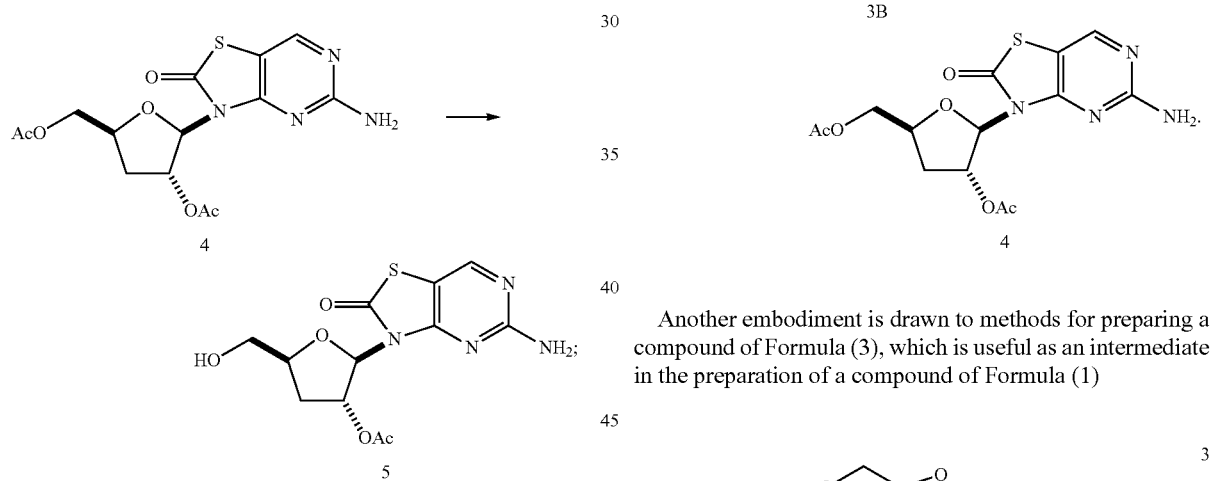

Another embodiment is drawn to methods for preparing a compound of Formula (3), which is useful as an intermediate in the preparation of a compound of Formula (1)

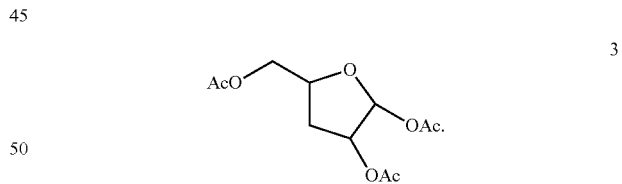

The method comprises:

(ii) sulfonating a compound of Formula (6) with a sulfonating agent in the presence of a base

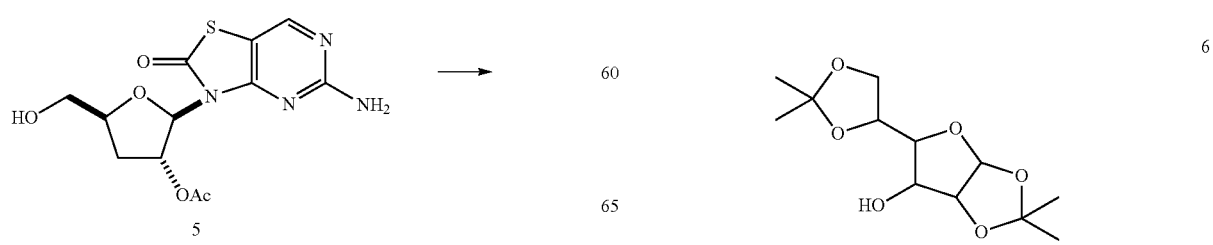

to form a sulfonyl substituted compound of Formula (7)

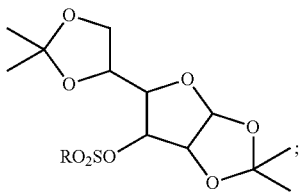
7 wherein R is an optionally substituted alkyl or aryl;
(iii) reducing the sulfonyl substituted compound of Formula (7) with a reducing agent to form a compound of Formula (8)

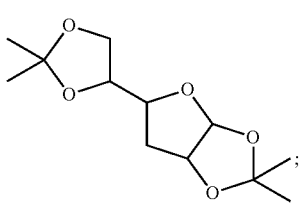
8

(iii) hydrolyzing the compound of Formula (8) with an acid to form a compound of Formula (9)

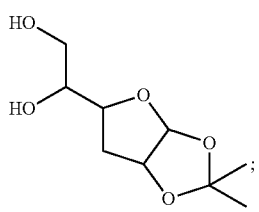
9

(iv) oxidizing the compound of Formula (9) with an oxidizing agent followed by reduction with a reducing agent to form a compound of Formula (101

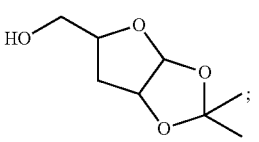
10 and
(v) acetylating the compound of Formula (10) with an acetylating agent in the presence of an acid catalyst to form the compound of Formula (3)

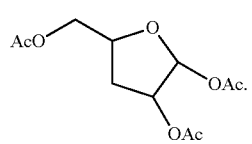
3

Another embodiment of the present disclosure is drawn to methods of preparing a compound of Formula (3B), which is useful as an intermediate in the preparation of a compound of Formula (1)

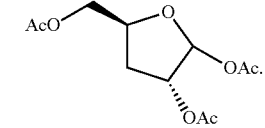
3B

The method comprises:
(i) sulfonating a compound of Formula (6B), Formula (6C), or mixtures thereof, with a sulfonating agent in the presence of a base

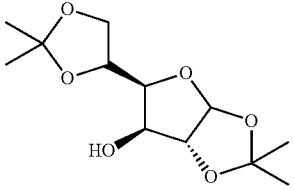
6B

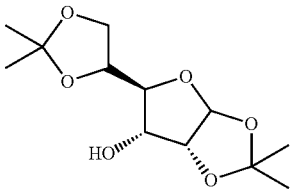
6C to form a sulfonyl substituted compound of Formula (7B), Formula (7C) or mixtures thereof,

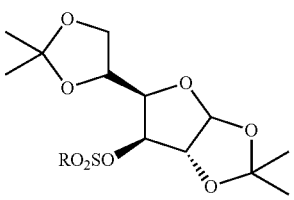
7B

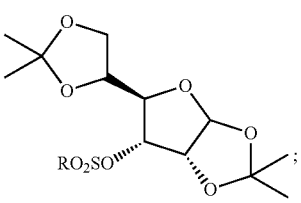
7C wherein R is an optionally substituted alkyl or aryl;
(ii) reducing the sulfonyl substituted compound of Formula (7B), Formula (7C), or mixtures thereof with a reducing agent to form a compound of Formula 8B

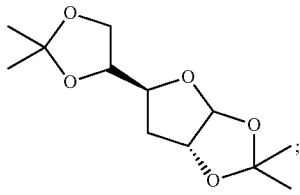
8B (iii) hydrolyzing the compound of Formula (8B) with an acid to form a compound of Formula (9B)

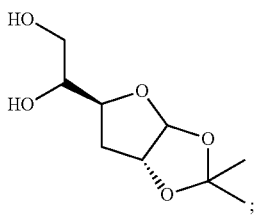
9B (iv) oxidizing the compound of Formula (9B) with an oxidizing agent followed by reduction with a reducing agent to form a compound of Formula (10B)

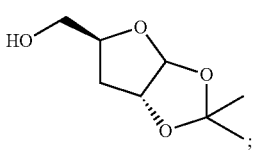
10B and (v) acetylating the compound of Formula (10B) with an acetylating agent in the presence of an acid catalyst to form the compound of Formula (3B)

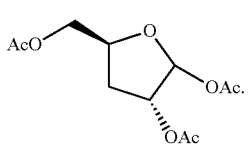
3B

In another embodiment, the disclosure relates to a method of reducing a sulfonyl substituted compound of Formula (7)

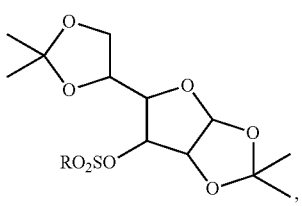
7 with a reducing agent to form a compound of Formula (8)

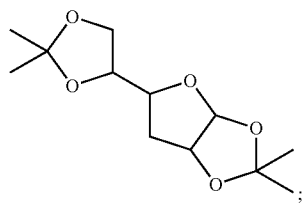
8 wherein R is an optionally substituted alkyl or aryl. In other embodiments, R is an optionally substituted $C_1$-$C_6$ alkyl or phenyl. In another embodiment, R is $CF_3$, $CH_3$, —$C_6H_4CH_3$.

In another embodiment, the disclosure relates to a method of reducing a sulfonyl substituted compound of Formula (7B), Formula (7C), or mixtures thereof,

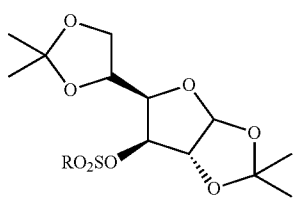
7B

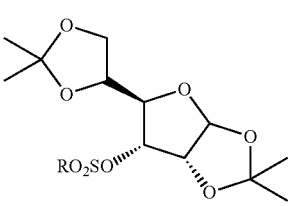
7C with a reducing agent to form a compound of Formula (8B)

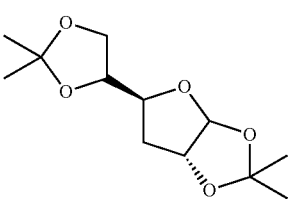
8B wherein R is an optionally substituted alkyl or aryl.

In other embodiments, R is an optionally substituted $C_1$-$C_6$ alkyl or phenyl. In another embodiment, R is $CF_3$, $CH_3$, or —$C_6H_4CH_3$.

The methods of the present disclosure are appropriate for the scalable commercial production of compounds described herein. The methods are operationally simple, robust and efficient. In particular, the methods are particularly useful for scaled-up production of p-toluene sulfonic acid salt of 5-amino-3-(2'-O-acetyl-3'-deoxy-β-D-ribofuranosyl)-3H-thiazolo[4,5-d]pyrimidin-2-one (1).

BRIEF DESCRIPTION OF THE DRAWINGS

FIG. 1 is a FT-Raman spectrum of a compound of Formula (1).

FIG. 2 is a PXRD (x-ray diffraction) pattern of a compound of Formula (1).

DETAILED DESCRIPTION OF THE DISCLOSURE

The term "comprising" (and its grammatical variations) as used herein is used in the inclusive sense of "having" or "including" and not in the exclusive sense of "consisting only of". The terms "a" and "the" as used herein are understood to encompass the plural as well as the singular.

As used herein, the term "halide" refers to fluoride, chloride, bromide and iodide. The term halogen refers to fluorine, chlorine, bromine and iodine.

The term "alkyl", as used herein, unless otherwise indicated, includes saturated monovalent hydrocarbon radicals having straight, branched, or cyclic moieties (including fused and bridged bicyclic and spirocyclic moieties), or a combination of the foregoing moieties. For an alkyl group to have cyclic moieties, the group must have at least three carbon atoms.

The term "aryl", as used herein, unless otherwise indicated, includes an organic radical derived from an aromatic hydrocarbon by removal of one hydrogen, such as phenyl or naphthyl.

The "alkyl" and "aryl" groups are optionally substituted by 1-5 substituents selected from —OH, halo, —CN, $C_1$-$C_6$ alkyl, arylalkyl, $C_1$-$C_6$ alkoxy, $C_1$-$C_6$ alkenyl, $C_1$-$C_6$ hydroxyl, $C_1$-$C_6$ hydroxyalkyl, amino, $C_1$-$C_6$ alkylamine, $C_1$-$C_6$ dialkylamine, wherein the alkyl groups can be further substituted with one or more halogens.

The term "Ac" means acetyl.

The compounds of the disclosure may exist as single stereoisomers, racemates and/or variable mixtures of enantiomers and/or diastereomers. All such single stereoisomers, racemates and/or variable mixtures of enantiomers and/or diastereomers are intended to be within the scope of the present disclosure.

As used herein, the term "oxidizing agent" refers to a substance or species that gains electrons in a chemical reaction and the term "reducing agent" refers to a substance that loses electrons in a chemical reaction.

The term "immunomodulator" refers to natural or synthetic products capable of modifying the normal or aberrant immune system through stimulation or suppression.

The term "preventing" refers to the ability of a compound or composition of the invention to prevent a disease identified herein in patients diagnosed as having the disease or who are at risk of developing such disease. The term also encompasses preventing further progression of the disease in patients who are already suffering from or have symptoms of such disease.

The term "patient" or "subject" means an animal (e.g., cow, horse, sheep, pig, chicken, turkey, quail, cat, dog, mouse, rat, rabbit, guinea pig, etc.) or a mammal, preferably a human, including chimeric and transgenic animals and mammals.

The term a "therapeutically effective amount" refers to an amount of the compound of the invention sufficient to provide a benefit in the treatment or prevention of disease, to delay or minimize symptoms associated with disease, or to cure or ameliorate the disease or infection or causes thereof. In particular, a therapeutically effective amount means an amount sufficient to provide a therapeutic benefit in vivo. Used in connection with an amount of a compound of the invention, the term preferably encompasses a non-toxic amount that improves overall therapy, reduces or avoids symptoms or causes of disease, or enhances the therapeutic efficacy of or synergies with another therapeutic agent.

The term a "prophylactically effective amount" refers to an amount of a compound of the invention or other active ingredient sufficient to result in the prevention of disease, recurrence or spread of a disease. A prophylactically effective amount may refer to an amount sufficient to prevent initial viral infection or the recurrence or spread of the infection or a disease associated with the infection. Used in connection with an amount of a compound of the invention, the term preferably encompasses a non-toxic amount that improves overall prophylaxis or enhances the prophylactic efficacy of or synergies with another prophylactic or therapeutic agent.

The term "in combination" refers to the use of more than one prophylactic and/or therapeutic agents simultaneously or sequentially and in a manner that their respective effects are additive or synergistic.

The term "treating" refers to:
(i) preventing a disease, disorder, or condition from occurring in an animal that may be predisposed to the disease, disorder and/or condition, but has not yet been diagnosed as having it;
(ii) inhibiting the disease, disorder, or condition, i.e., arresting its development; and
(iii) relieving the disease, disorder, or condition, or relieving the symptoms of the disease, disorder, or condition and/or causing regression of the disease, disorder, or condition.

The terms "R" and "S" indicate the specific stereochemical configuration of a substituent at an asymmetric carbon atom in a chemical structure as drawn.

The compounds of the invention may exhibit the phenomenon of tautomerism. While the formulae set forth herein cannot expressly depict all possible tautomeric forms, it is to be understood that the formulae set forth herein are intended to represent any tautomeric form of the depicted compound and is not to be limited merely to a specific compound form depicted by the formula drawings.

As generally understood by those skilled in the art, an optically pure compound having one chiral center (i.e., one asymmetric carbon atom) is one that consists essentially of one of the two possible enantiomers (i.e., is enantiomerically pure), and an optically pure compound having more than one chiral center is one that is both diastereomerically pure and enantiomerically pure. Preferably, the compounds of the present invention are used in a form that is at least 90% free of other enantiomers or diastereomers of the compounds, that is, a form that contains at least 90% of a single isomer (80% enantiomeric excess ("e.e.") or diastereomeric excess ("d.e.")), more preferably at least 95% (90% e.e. or d.e.), even more preferably at least 97.5% (95% e.e. or d.e.), and most preferably at least 99% (98% e.e. or d.e.).

P-toluene sulfonic acid salt of 5-amino-3-(2'-O-acetyl-3'-deoxy-beta-D-ribofuranosyl)-3H-thiazolo[4,5-d]pyrimidin-2-one is shown below in Formula (1)

1

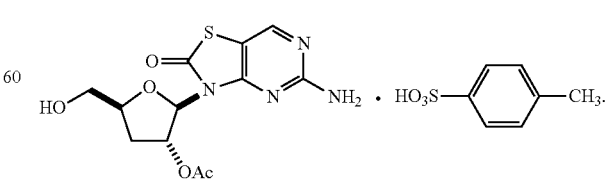

The free base of 5-amino-3-(2'-O-acetyl-3'-deoxy-beta-D-ribofuranosyl)-3H-thiazolo[4,5-d]pyrimidin-2-one (5) is an amorphous substance. Prior to the present invention, 5-amino-3-(2'-O-acetyl-3'-deoxy-beta-D-ribofuranosyl)-3H-thiazolo[4,5-d]pyrimidin-2-one (5) had never been recovered in crystalline form. It has now been surprisingly found in accordance with the present disclosure that under certain conditions a crystalline form with very low residual solvent can be obtained from the p-toluene sulfonic acid salt of 5-amino-3-(2'-O-acetyl-3'-deoxy-beta-D-ribofuranosyl)-3H-thiazolo[4,5-d]pyrimidin-2-one (1). The crystalline form of the present invention has advantageous properties over the amorphous form of 5-amino-3-(2'-O-acetyl-3'-deoxy-beta-D-ribofuranosyl)-3H-thiazolo[4,5-d]pyrimidin-2-one (5). For example, less solvent residue is present in the ultimate drug substance in any form, such as a dissolved state. In addition, additional purification is effected by the crystallization process. This results in higher stability of the drug substance and easier handling in the production plant.

The free base of 5-amino-3-(2'-O-acetyl-3'-deoxy-beta-D-ribofuranosyl)-3H-thiazolo[4,5-d]pyrimidin-2-one (5) is a hydroscopic substance. From the chemical structure it is expected that 5-amino-3-(2'-O-acetyl-3'-deoxy-beta-D-ribofuranosyl)-3H-thiazolo[4,5-d]pyrimidin-2-one (5) may be very sensitive to hydrolysis. It has now been surprisingly found in accordance with the present disclosure that the crystalline form of the p-toluene sulfonic salt is only slightly hygroscopic thus having better storage properties and being easier to process.

The free base of 5-amino-3-(2'-O-acetyl-3'-deoxy-beta-D-ribofuranosyl)-3H-thiazolo[4,5-d]pyrimidin-2-one (5) has been found to contain some related substances (side reactions during synthesis) and shows residual solvents and water. The term "essentially pure" in accordance with the present invention means that the sum of related substances is less than 1%, preferably less than 0.75%, more preferably less than 0.5% and that the residual solvents and water are less than 1%, preferably less than 0.75%, more preferably less than 0.5% and still more preferably less than 0.25% by weight.

IR data—FIG. 1 shows a FT-Raman spectrum of the compound of Formula (1). The compound of Formula (1) is characterized by the following major IR bands at 1356, 1130, 804, 498 and 435 cm$^{-1}$ with medium bands at 1637, 1602, 1054, 1037, 609 and 530 cm$^{-1}$.

X-ray data—FIG. 2 shows a x-ray diffraction diagram of the compound of Formula (1). In the x-ray diagram, the angle of diffraction 2theta is plotted on the x-axis and the peak intensity is plotted on the y-axis. The strongest line in the x-ray diffraction diagram is observed at an angle of 5.5°±0.3° with lesser intensity lines at 11.8°, 12.3°, 17.9°, 18.2°, 19.7°, 20.2°, 21.3°, 21.9°, 23.8°, 24.1° and 25.9°±0.3°.

Pharmaceutical Compositions

The crystalline compound of Formula (1) is used to prepare pharmaceutical compositions comprising at least one pharmaceutically acceptable carrier and the compound of Formula (1). Details for preparing pharmaceutical compositions using a carrier are described in U.S. Patent Application Publication No. 2006/0160830 (U.S. application Ser. No. 11/304, 691), which is incorporated herein by reference in its entirety.

Pharmaceutical compositions and single unit dosage forms comprising a compound of Formula (1), or a pharmaceutically hydrate or solvate thereof, are also encompassed by the disclosure. Individual dosage forms of the disclosure may be suitable for oral, mucosal (including sublingual, buccal, rectal, nasal, or vaginal), parenteral (including subcutaneous, intramuscular, bolus injection, intraarterial, or intravenous), transdermal, or topical administration. Pharmaceutical compositions and dosage forms of the disclosure typically also comprise one or more pharmaceutically acceptable excipients. Sterile dosage forms are also contemplated. In an alternative embodiment, pharmaceutical compositions encompassed by this embodiment include a compound of Formula (1), or a pharmaceutically acceptable hydrate or solvate thereof, and at least one additional therapeutic agent.

The composition, shape, and type of dosage forms of the disclosure will typically vary depending on their use. For example, a dosage form used in the acute treatment of a disease or a related disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease or disorder. These and other ways in which specific dosage forms encompassed by this disclosure will vary from one another will be readily apparent to those skilled in the art. See, e.g., *Remington's Pharmaceutical Sciences,* 18th ed., Mack Publishing, Easton Pa. (1990). Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

Typical pharmaceutical compositions and dosage forms comprise one or more carriers, excipients or diluents. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form.

The disclosure encompasses anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Carstensen, *Drug Stability: Principles & Practice,* 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms of the disclosure can be prepared using anhydrous or low moisture containing ingredients and low moisture or low humidity conditions.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The disclosure further encompasses pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients. However, typical dosage forms of the disclosure comprises a compound of Formula (1) or hydrate thereof comprise 0.1 mg to 1500 mg per unit to provide doses of about 0.01 to 200 mg/kg per day.

Oral Dosage Forms

Pharmaceutical compositions of the disclosure that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, *Remington's Pharmaceutical Sciences,* 18th ed., Mack Publishing, Easton Pa. (1990).

Typical oral dosage forms of the disclosure are prepared by combining the active ingredient(s) in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms of the disclosure include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the disclosure is typically present in from about 50 to about 99 weight percent of the pharmaceutical composition or dosage form.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. A specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Disintegrants are used in the compositions of the disclosure to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the disclosure. The amount of disintegrant used varies based upon the type of formulation, and is readily discernible to those of ordinary skill in the art. Typical pharmaceutical compositions comprise from about 0.5 to about 15 weight percent of disintegrant, specifically from about 1 to about 5 weight percent of disintegrant.

Disintegrants that can be used in pharmaceutical compositions and dosage forms of the disclosure include, but are not limited to, agar-agar, alginic acid, calcium carbonate, microcrystalline cellulose, croscarmellose sodium, crospovidone, polacrilin potassium, sodium starch glycolate, potato or tapioca starch, pre-gelatinized starch, other starches, clays, other algins, other celluloses, gums, and mixtures thereof.

Lubricants that can be used in pharmaceutical compositions and dosage forms of the disclosure include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

Delayed Release Dosage Forms

Active ingredients of the disclosure can be administered by controlled release means or by delivery devices that are well known to those of ordinary skill in the art. Examples include, but are not limited to, those described in U.S. Pat. Nos. 3,845, 770; 3,916,899; 3,536,809; 3,598,123; and 4,008,719, 5,674, 533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients of the disclosure. The disclosure thus encompasses single unit dosage forms suitable for oral administration such as, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

Parenteral Dosage Forms

Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are preferably sterile or capable of being sterilized prior to administration to a patient. Examples of parenteral dosage forms include, but are not limited to, solutions ready for injection, dry and/or lyophilized products ready to be dissolved or suspended in a pharmaceutically acceptable vehicle for injection (reconstitutable powders), suspensions ready for injection, and emulsions.

Suitable vehicles that can be used to provide parenteral dosage forms of the disclosure are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms of the disclosure.

Transdermal Dosage Forms

Transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal and topical dosage forms encompassed by this disclosure are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof.

Depending on the specific tissue to be treated, additional components may be used prior to, in conjunction with, or subsequent to treatment with active ingredients of the disclosure. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

Topical Dosage Forms

Topical dosage forms of the disclosure include, but are not limited to, creams, lotions, ointments, gels, solutions, emulsions, suspensions, or other forms known to one of skill in the art. See, e.g., *Remington's Pharmaceutical Sciences*, 18th eds., Mack Publishing, Easton Pa. (1990); and *Introduction to Pharmaceutical Dosage Forms*, 4th ed., Lea & Febiger, Philadelphia (1985).

Suitable excipients (e.g., carriers and diluents) and other materials that can be used to provide transdermal and topical dosage forms encompassed by this disclosure are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof.

Depending on the specific tissue to be treated, additional components may be used prior to, in conjunction with, or subsequent to treatment with active ingredients of the disclosure. For example, penetration enhancers can be used to assist in delivering the active ingredients to the tissue. Suitable penetration enhancers include, but are not limited to: acetone;

various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

Mucosal Dosage Forms

Mucosal dosage forms of the disclosure include, but are not limited to, ophthalmic solutions, sprays and aerosols, or other forms known to one of skill in the art. See, e.g., *Remington's Pharmaceutical Sciences*, 18th eds., Mack Publishing, Easton Pa. (1990); and *Introduction to Pharmaceutical Dosage Forms*, 4th ed., Lea & Febiger, Philadelphia (1985). Dosage forms suitable for treating mucosal tissues within the oral cavity can be formulated as mouthwashes or as oral gels. In one embodiment, the aerosol comprises a carrier. In another embodiment, the aerosol is carrier free.

The compound of Formula (1) also be administered directly to the lung by inhalation. For administration by inhalation, a compound of Formula (1) be conveniently delivered to the lung by a number of different devices. For example, a Metered Dose Inhaler ("MDI") which utilizes canisters that contain a suitable low boiling propellant, e.g., dichlorodifluoromethane, trichlorofluoromethane, dichlorotetrafluoroethane, carbon dioxide or other suitable gas can be used to deliver a Formula (1) compound directly to the lung. MDI devices are available from a number of suppliers such as 3M Corporation, Aventis, Boehringer Ingleheim, Forest Laboratories, Glaxo-Wellcome, Schering Plough and Vectura.

Alternatively, a Dry Powder Inhaler (DPI) device can be used to administer a Formula (1) compound to the lung (see, e.g., Raleigh et al., *Proc. Amer. Assoc. Cancer Research Annual Meeting*, 1999, 40, 397, which is herein incorporated by reference). DPI devices typically use a mechanism such as a burst of gas to create a cloud of dry powder inside a container, which can then be inhaled by the patient. DPI devices are also well known in the art and can be purchased from a number of vendors which include, for example, Fisons, Glaxo-Wellcome, Inhale Therapeutic Systems, ML Laboratories, Qdose and Vectura. A popular variation is the multiple dose DPI ("MDDPI") system, which allows for the delivery of more than one therapeutic dose. MDDPI devices are available from companies such as AstraZeneca, GlaxoWellcome, IVAX, Schering Plough, SkyePharma and Vectura. For example, capsules and cartridges of gelatin for use in an inhaler or insufflator can be formulated containing a powder mix of the compound and a suitable powder base such as lactose or starch for these systems.

Another type of device that can be used to deliver a Formula (1) compound to the lung is a liquid spray device supplied, for example, by Aradigm Corporation. Liquid spray systems use extremely small nozzle holes to aerosolize liquid drug formulations that can then be directly inhaled into the lung.

In one embodiment, a nebulizer device is used to deliver a compound of Formula (1) to the lung. Nebulizers create aerosols from liquid drug formulations by using, for example, ultrasonic energy to form fine particles that can be readily inhaled (See e.g., Verschoyle et al., *British J. Cancer*, 1999, 80, Suppl 2, 96, which is herein incorporated by reference). Examples of nebulizers include devices supplied by Sheffield/Systemic Pulmonary Delivery Ltd. (See, Armer et al., U.S. Pat. No. 5,954,047; van der Linden et al., U.S. Pat. No. 5,950,619; van der Linden et al., U.S. Pat. No. 5,970,974, which are herein incorporated by reference), Aventis and Batelle Pulmonary Therapeutics.

In one embodiment, an electrohydrodynamic ("EHD") aerosol device is used to deliver Formula (1) compounds to the lung. EHD aerosol devices use electrical energy to aerosolize liquid drug solutions or suspensions (see, e.g., Noakes et al., U.S. Pat. No. 4,765,539; Coffee, U.S. Pat. No. 4,962,885; Coffee, PCT Application, WO 94/12285; Coffee, PCT Application, WO 94/14543; Coffee, PCT Application, WO 95/26234, Coffee, PCT Application, WO 95/26235, Coffee, PCT Application, WO 95/32807, which are herein incorporated by reference). The electrochemical properties of a compound of Formula (1) formulation may be important parameters to optimize when delivering this drug to the lung with an EHD aerosol device and such optimization is routinely performed by one of skill in the art. EHD aerosol devices may more efficiently delivery drugs to the lung than existing pulmonary delivery technologies. Other methods of intra-pulmonary delivery of a compound of Formula (1) will be known to the skilled artisan and are within the scope of the disclosure.

Liquid drug formulations suitable for use with nebulizers and liquid spray devices and EHD aerosol devices will typically include a compound of Formula (1) compound with a pharmaceutically acceptable carrier. Preferably, the pharmaceutically acceptable carrier is a liquid such as alcohol, water, polyethylene glycol or a perfluorocarbon. Optionally, another material may be added to alter the aerosol properties of the solution or suspension of a compound of Formula (1). Preferably, this material is liquid such as an alcohol, glycol, polyglycol or a fatty acid. Other methods of formulating liquid drug solutions or suspension suitable for use in aerosol devices are known to those of skill in the art (see, e.g., Biesalski, U.S. Pat. Nos. 5,112,598; Biesalski, 5,556,611, which are herein incorporated by reference). A compound of Formula (1) can also be formulated in rectal or vaginal compositions such as suppositories or retention enemas, e.g., containing conventional suppository bases such as cocoa butter or other glycerides.

In addition to the formulations described previously, a compound of Formula (1) can also be formulated as a depot preparation. Such long acting formulations can be administered by implantation (for example subcutaneously or intramuscularly) or by intramuscular injection. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt.

Alternatively, other pharmaceutical delivery systems can be employed. Liposomes and emulsions are well known examples of delivery vehicles that can be used to deliver the compound of Formula (1). Certain organic solvents such as dimethylsulfoxide can also be employed, although usually at the cost of greater toxicity. A compound of Formula (1) can also be delivered in a controlled release system. In one embodiment, a pump can be used (Sefton, *CRC Crit. Ref Biomed Eng.*, 1987, 14, 201; Buchwald et al., Surgery, 1980, 88, 507; Saudek et al., *N. Engl. J. Med.*, 1989, 321, 574). In another embodiment, polymeric materials can be used (see *Medical Applications of Controlled Release*, Langer and Wise (eds.), CRC Pres., Boca Raton, Fla. (1974); *Controlled Drug Bioavailability, Drug Product Design and Performance*, Smolen and Ball (eds.), Wiley, New York (1984); Ranger and Peppas, *J. Macromol. Sci. Rev. Macromol. Chem.*, 1983, 23, 61; see also Levy et al., *Science*, 1985, 228, 190; During et al., *Ann. Neurol.*, 1989, 25,351; Howard et al., *J. Neurosurg.*, 71, 105 (1989). In yet another embodiment, a controlled-release system can be placed in proximity of the target of the compounds of the disclosure, e.g., the lung, thus requiring only a fraction of the systemic dose (see, e.g., Goodson, in *Medical Applications of Controlled Release*, supra, vol. 2, pp. 115 (1984)). Other controlled-release system can be used (see, e.g., Langer, *Science*, 1990, 249, 1527).

Suitable excipients (e.g., carriers and diluents) and other materials that can be used to provide mucosal dosage forms encompassed by this disclosure are well known to those skilled in the pharmaceutical arts, and depend on the particular site or method which a given pharmaceutical composition or dosage form will be administered. With that fact in mind, typical excipients include, but are not limited to, water, ethanol, ethylene glycol, propylene glycol, butane-1,3-diol, isopropyl myristate, isopropyl palmitate, mineral oil, and mixtures thereof, which are non-toxic and pharmaceutically acceptable. Examples of such additional ingredients are well known in the art. See, e.g., Remington's Pharmaceutical Sciences, 18th eds., Mack Publishing, Easton Pa. (1990).

The pH of a pharmaceutical composition or dosage form, or of the tissue to which the pharmaceutical composition or dosage form is applied, can also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

Kits

The disclosure provides a pharmaceutical pack or kit comprising one or more containers comprising a compound of Formula (1) useful for the treatment or prevention of disease. In other embodiments, the disclosure provides a pharmaceutical pack or kit comprising one or more containers comprising a compound of Formula (1) useful for the treatment or prevention of disease and one or more containers comprising an additional therapeutic agent.

The disclosure also provides a pharmaceutical pack or kit comprising one or more containers comprising one or more of the ingredients of the pharmaceutical compositions of the disclosure. Optionally associated with such container(s) can be a notice in the form prescribed by a governmental agency regulating the manufacture, use or sale of pharmaceuticals or biological products, which notice reflects approval by the agency of manufacture, use or sale for human administration.

Treating Disease

In one embodiment, a compound of Formula (1) is used in methods of treating or preventing disease. For instance, methods are provided for preventing or treating infections of a warm-blooded animal, especially a human, by a pathogenic organism comprising administering an effective amount of a crystalline form of a compound of Formula (1). In a preferred embodiment the pathogenic organism is a bacterial, fungal or viral infection disclosed in WO2005/121162, in a preferred embodiment a viral infection caused by adenovirus, cytomegalovirus, hepatitis A virus (HAV), hepatitis B virus (HBV), flaviviruses including Yellow Fever virus and hepatitis C virus (HCV), herpes simplex type I and 2, herpes zoster, human herpesvirus 6, human immunodeficiency virus (HIV), human papilloma virus (HPV), influenza A virus, influenza B virus, measles, parainfluenza virus, poliovirus, poxvirus (including smallpox and monkeypod virus), rhinovirus, respiratory syncytial virus (RSV), multiple families of viruses that cause hemorrhagic fevers, including the Arenaviruses (LCM, Junin virus, Machup virus, Guanarito virus, and Lassa Fever), the Bunyaviruses (Hanta viruses and Rift Valley Fever) and Filoviruses (Ebola and Marburg virus), a range of viral encephalitides including West Nile virus, LaCrosse virus, California Encephalitis virus, Venezuelan Equine Encephalitis virus, Eastern Equine Encephalitis virus, Western Equine Encephalitis virus, Japanese Encephalitis virus, Kysanur Forest virus, and tickborne viruses such as Crimean-Congo Hemorrhagic fever virus. Particularly preferred are HBV and HCV.

Another embodiment provides methods of modulating immune cytokine activities of a warm-blooded animal, especially a human, comprising administering an effective amount of a crystalline form of the compound of Formula (1). Also provided is a crystalline form of the compound of Formula (1) for use in medicine. Also provided is the use of a crystalline form Formula (1) for the manufacture of a medicament for the treatment of an infection by a pathogen, especially a virus, e.g. HCV or HBV.

Another embodiment provides methods of treating tumors or cancer in mammals by administrating to the mammal (patient) a therapeutically effective amount of the compound of Formula (1). Tumors or cancers contemplated to be treated include but are not limited to those caused by virus, and the effect may involve inhibiting the transformation of virus-infected cells to a neoplastic state, inhibiting the spread of viruses from transformed cells to other normal cells, and/or arresting the growth of virus-transformed cells. The compound of the disclosure is expected to be useful against a broad spectrum of tumors including but not limited to carcinomas, sarcomas, and leukemias. Included in such a class are mammary, colon, bladder, lung, prostate, stomach, and pancreas carcinomas and lymphoblastic and myeloid leukemias.

The magnitude of a prophylactic or therapeutic dose of a compound of Formula (1), or a pharmaceutically acceptable solvate or hydrate thereof in the acute or chronic treatment or prevention of an infection will vary, however, with the nature and severity of the infection, and the route by which the active ingredient is administered. The dose, and in some cases the dose frequency, will also vary according to the disease to be treated, the age, body weight, and response of the individual patient. Suitable dosing regimens can be readily selected by those skilled in the art with due consideration of such factors.

The methods of the present disclosure are particularly well suited for human patients. In particular, the methods and doses of the present disclosure can be useful for immunocompromised patients including, but not limited to cancer patients, HIV infected patients, and patients with an immunodegenerative disease. Furthermore, the methods can be useful for immunocompromised patients currently in a state of remission. The methods and doses of the present disclosure are also useful for patients undergoing other antiviral treatments. The prevention methods of the present disclosure are particularly useful for patients at risk of viral infection. These patients include, but are not limited to health care workers, e.g., doctors, nurses, hospice care givers; military personnel; teachers; childcare workers; patients traveling to, or living in, foreign locales, in particular third world locales including social aid workers, missionaries, and foreign diplomats. Finally, the methods and compositions include the treatment of refractory patients or patients resistant to treatment such as resistance to reverse transcriptase inhibitors, protease inhibitors, etc.

Doses

Toxicity and efficacy of a compound of Formula (1) can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$.

The data obtained from the cell culture assays and animal studies can be used in formulating a range of dosage of the compounds for use in humans. The dosage of such compounds lie preferably within a range of circulating concentrations that include the $ED_{50}$ with little or no toxicity. The dosage may vary within this range depending upon the dosage form employed and the route of administration utilized. For any compound used in the method of the disclosure, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture; alternatively, the dose of a compound of Formula (1) may be formulated in animal models to achieve a circulating plasma concentration range of the compound that corresponds to the concentration required to achieve a fixed magnitude of response. Such information can be used to more accurately determine useful doses in humans. Levels in plasma may be measured, for example, by high performance liquid chromatography.

The protocols and compositions of the disclosure are preferably tested in vitro, and then in vivo, for the desired therapeutic or prophylactic activity, prior to use in humans. For example, in vitro assays which can be used to determine whether administration of a specific therapeutic protocol is indicated, include in vitro cell culture assays in which cells that are responsive to the effects of a compound of Formula (1) are exposed to the ligand and the magnitude of response is measured by an appropriate technique. The assessment of a compounds of Formula (1) is then evaluated with respect to its potency. Compounds for use in methods of the disclosure can be tested in suitable animal model systems prior to testing in humans, including but not limited to in rats, mice, chicken, cows, monkeys, rabbits, hamsters, etc. The compounds can then be used in the appropriate clinical trials.

The magnitude of a prophylactic or therapeutic dose of a compound of Formula (1) of the disclosure or a pharmaceutically acceptable solvate or hydrate thereof in the acute or chronic treatment or prevention of an infection or condition will vary with the nature and severity of the infection, and the route by which the active ingredient is administered. The dose, and perhaps the dose frequency, will also vary according to the disease to be treated, the age, body weight, and response of the individual patient. Suitable dosing regimens can be readily selected by those skilled in the art with due consideration of such factors. In one embodiment, the dose administered depends upon the specific compound to be used, and the weight and condition of the patient. Suitable doses can be predicted on the basis of the aforementioned in vitro measurements and on the basis of animal studies. In general, the dose per day is in the range of from about 0.001 to 100 mg/kg, preferably about 1 to 25 mg/kg, more preferably about 5 to 15 mg/kg. For treatment of humans infected by hepatitis C viruses, about 0.1 mg to about 15 g per day is administered in about one to four divisions a day, preferably 100 mg to 12 g per day, more preferably from 100 mg to 8000 mg per day.

Additionally, the recommended daily dose ran can be administered in cycles as single agents or in combination with other therapeutic agents. In one embodiment, the daily dose is administered in a single dose or in equally divided doses. In a related embodiment, the recommended daily dose can be administered once time per week, two times per week, three times per week, four times per week or five times per week.

In one embodiment, the compounds of the disclosure are administered to provide systemic distribution of the compound within the patient. In a related embodiment, the compounds of the disclosure are administered to produce a systemic effect in the body.

In another embodiment the compounds of the disclosure are administered via oral, mucosal (including sublingual, buccal, rectal, nasal, or vaginal), parenteral (including subcutaneous, intramuscular, bolus injection, intraarterial, or intravenous), transdermal, or topical administration. In a specific embodiment the compounds of the disclosure are administered via mucosal (including sublingual, buccal, rectal, nasal, or vaginal), parenteral (including subcutaneous, intramuscular, bolus injection, intraarterial, or intravenous), transdermal, or topical administration. In a further specific embodiment, the compounds of the disclosure are administered via oral administration. In a further specific embodiment, the compounds of the disclosure are not administered via oral administration.

Different therapeutically effective amounts may be applicable for different infections, as will be readily known by those of ordinary skill in the art. Similarly, amounts sufficient to treat or prevent such infections, but insufficient to cause, or sufficient to reduce, adverse effects associated with conventional therapies are also encompassed by the above described dosage amounts and dose frequency schedules.

Combination Therapy

Specific methods of the disclosure further comprise the administration of an additional therapeutic agent (i.e., a therapeutic agent other than a compound of the disclosure). In certain embodiments of the present disclosure, the compounds of the disclosure can be used in combination with at least one other therapeutic agent. Therapeutic agents include, but are not limited to antibiotics, antiemetic agents, antidepressants, and antifungal agents, anti-inflammatory agents, antiviral agents, anticancer agents, immunomodulatory agents, α-interferons, β-interferons, ribavirin, alkylating agents, hormones, cytokines, or toll receptor-like modulators.

The compound of Formula (1) can be administered or formulated in combination with antibiotics. For example, they can be formulated with a macrolide (e.g., tobramycin (Tobi®)), a cephalosporin (e.g., cephalexin (Keflex®), cephradine (Velosef®), cefuroxime (Ceftin®), cefprozil (Cefzil®), cefaclor (Ceclor®), cefixime (Suprax®) or cefadroxil (Duricef®)), a clarithromycin (e.g., clarithromycin (Biaxin®)), an erythromycin (e.g., erythromycin (EMycin®)), a penicillin (e.g., penicillin V (V-Cillin K® or Pen Vee K®)) or a quinolone (e.g., ofloxacin (Floxin®), ciprofloxacin (Cipro®) or norfloxacin (Noroxin®)), aminoglycoside antibiotics (e.g., apramycin, arbekacin, bambermycins, butirosin, dibekacin, neomycin, neomycin, undecylenate, netilmicin, paromomycin, ribostamycin, sisomicin, and spectinomycin), amphenicol antibiotics (e.g., azidamfenicol, chloramphenicol, florfenicol, and thiamphenicol), ansamycin antibiotics (e.g., rifamide and rifampin), carbacephems (e.g., loracarbef), carbapenems (e.g., biapenem and imipenem), cephalosporins (e.g., cefaclor, cefadroxil, cefamandole, cefatrizine, cefazedone, cefozopran, cefpimizole, cefpiramide, and cefpirome), cephamycins (e.g., cefbuperazone, cefinetazole, and cefminox), monobactams (e.g., aztreonam, carumonam, and tigemonam), oxacephems (e.g., flomoxef, and moxalactam), penicillins (e.g., amdinocillin, amdinocillin pivoxil, amoxicillin, bacampicillin, benzylpenicillinic acid, benzylpenicillin sodium, epicillin, fenbenicillin, floxacillin, penamccillin, penethamate hydriodide, penicillin o-benethamine, penicillin 0, penicillin V, penicillin V benzathine, penicillin V hydrabamine, penimepicycline, and phencihicillin potassium), lincosamides (e.g., clindamycin, and lincomycin), amphomycin, bacitracin, capreomycin, colistin, enduracidin, enviomycin, tetracyclines (e.g., apicycline, chlortetracycline, clomocycline, and demeclocycline), 2,4-diaminopyrimidines (e.g., brodimoprim), nitrofurans (e.g., furaltadone, and furazolium chloride), quinolones and analogs thereof (e.g., cinoxacin, clinafloxacin, flumequine, and grepagloxacin), sulfonamides (e.g., acetyl sulfamethoxypyrazine, benzylsulfamide, noprylsulfamide, phthalylsulfacetamide, sulfachrysoidine, and sulfacytine), sulfones (e.g., diathymosulfone, glucosulfone sodium, and solasulfone), cycloserine, mupirocin and tuberin.

A compound of Formula (1) can also be administered or formulated in combination with an antiemetic agent. Suitable antiemetic agents include, but are not limited to, metoclopromide, domperidone, prochlorperazine, promethazine, chlorpromazine, trimethobenzamide, ondansetron, granisetron, hydroxyzine, acethylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinols, thiethylperazine, thioproperazine, tropisetron, and mixtures thereof.

The compound of Formula (1) can be administered or formulated in combination with an antidepressant. Suitable antidepressants include, but are not limited to, binedaline, caroxazone, citalopram, dimethazan, fencamine, indalpine, indeloxazine hydrocholoride, nefopam, nomifensine, oxitriptan, oxypertine, paroxetine, sertraline, thiazesim, trazodone, benmoxine, iproclozide, iproniazid, isocarboxazid, nialamide, octamoxin, phenelzine, cotinine, rolicyprine, rolipram, maprotiline, metralindole, mianserin, mirtazepine, adinazolam, amitriptyline, amitriptylinoxide, amoxapine, butriptyline, clomipramine, demexiptiline, desipramine, dibenzepin, dimetacrine, dothiepin, doxepin, fluacizine, imipramine, imipramine N-oxide, iprindole, lofepramine, melitracen, metapramine, nortriptyline, noxiptilin, opipramol, pizotyline, propizepine, protriptyline, quinupramine, tianeptine, trimipramine, adrafinil, benactyzine, bupropion, butacetin, dioxadrol, duloxetine, etoperidone, febarbamate, femoxetine, fenpentadiol, fluoxetine, fluvoxamine, hematoporphyrin, hypericin, levophacetoperane, medifoxamine, milnacipran, minaprine, moclobemide, nefazodone, oxaflozane, piberaline, prolintane, pyrisuccideanol, ritanserin, roxindole, rubidium chloride, sulpiride, tandospirone, thozalinone, tofenacin, toloxatone, tranylcypromine, L-tryptophan, venlafaxine, viloxazine, and zimeldine.

The compound of Formula (1) can be administered or formulated in combination with an antifungal agent. Suitable antifungal agents include but are not limited to amphotericin B, itraconazole, ketoconazole, fluconazole, intrathecal, flucytosine, miconazole, butoconazole, clotrimazole, nystatin, terconazole, tioconazole, ciclopirox, econazole, halopgrin, naftifine, terbinafine, undecylenate, and griseofulvin.

The compound of Formula (1) can be administered or formulated in combination with an anti-inflammatory agent. Useful anti-inflammatory agents include, but are not limited to, non-steroidal anti-inflammatory drugs such as salicylic acid, acetylsalicylic acid, methyl salicylate, diflunisal, salsalate, olsalazine, sulfasalazine, acetaminophen, indomethacin, sulindac, etodolac, mefenamic acid, meclofenamate sodium, tolmetin, ketorolac, dichlofenac, ibuprofen, naproxen, naproxen sodium, fenoprofen, ketoprofen, flurbinprofen, oxaprozin, piroxicam, meloxicam, ampiroxicam, droxicam, pivoxicam, tenoxicam, nabumetome, phenylbutazone, oxyphenbutazone, antipyrine, aminopyrine, apazone and nimesulide; leukotriene antagonists including, but not limited to, zileuton, aurothioglucose, gold sodium thiomalate and auranofin; steroids including, but not limited to, alclometasone diproprionate, amcinonide, beclomethasone dipropionate, betametasone, betamethasone benzoate, betamethasone diproprionate, betamethasone sodium phosphate, betamethasone valerate, clobetasol proprionate, clocortolone pivalate, hydrocortisone, hydrocortisone derivatives, desonide, desoximatasone, dexamethasone, flunisolide, flucoxinolide, flurandrenolide, halcinocide, medrysone, methylprednisolone, methprednisolone acetate, methylprednisolone sodium succinate, mometasone furoate, paramethasone acetate, prednisolone, prednisolone acetate, prednisolone sodium phosphate, prednisolone tebuatate, prednisone, triamcinolone, triamcinolone acetonide, triamcinolone diacetate, and triamcinolone hexacetonide; and other anti-inflammatory agents including, but not limited to, methotrexate, colchicine, allopurinol, probenecid, sulfinpyrazone and benzbromarone.

The compound of Formula (1) can be administered or formulated in combination with another antiviral agent. Useful antiviral agents include, but are not limited to, protease inhibitors, nucleoside reverse transcriptase inhibitors, non-nucleoside reverse transcriptase inhibitors and nucleoside analogs. The antiviral agents include but are not limited to zidovudine, acyclovir, gangcyclovir, vidarabine, idoxuridine, trifluridine, levovirin, viramidine and ribavirin, as well as foscarnet, amantadine, rimantadine, saquinavir, indinavir, amprenavir, lopinavir, ritonavir, the α-interferons; β-interferons; adefovir, clevadine, entecavir, pleconaril.

The compound of Formula (1) can be administered or formulated in combination with an immunomodulatory agent. Immunomodulatory agents include, but are not limited to, methothrexate, leflunomide, cyclophosphamide, cyclosporine A, mycophenolate mofetil, rapamycin (sirolimus), mizoribine, deoxyspergualin, brequinar, malononitriloamindes (e.g., leflunamide), T cell receptor modulators, and cytokine receptor modulators, peptide mimetics, and antibodies (e.g., human, humanized, chimeric, monoclonal, polyclonal, Fvs, ScFvs, Fab or F(ab)$_2$ fragments or epitope binding fragments), nucleic acid molecules (e.g., antisense nucleic acid molecules and triple helices), small molecules, organic compounds, and inorganic compounds. Examples of T cell receptor modulators include, but are not limited to, anti-T cell receptor antibodies (e.g., anti-CD4 antibodies (e.g., cM-T412 (Boehringer), IDEC-CE9.1® (IDEC and SKB), mAB 4162W94, Orthoclone and OKTcdr4a (Janssen-Cilag)), anti-CD3 antibodies (e.g., Nuvion (Product Design Labs), OKT3 (Johnson & Johnson), or Rituxan (IDEC)), anti-CD5 antibodies (e.g., an anti-CD5 ricin-linked immunoconjugate), anti-CD7 antibodies (e.g., CHH-380 (Novartis)), anti-CD8 antibodies, anti-CD40 ligand monoclonal antibodies (e.g., IDEC-131 (IDEC)), anti-CD52 antibodies (e.g., CAMPATH 1H (Ilex)), anti-CD2 antibodies, anti-CD11a antibodies (e.g., Xanelim (Genentech)), anti-B7 antibodies (e.g., IDEC-114 (IDEC)), CTLA4-immunoglobulin, and toll receptor-like (TLR) modulators. Examples of cytokine receptor modulators include, but are not limited to, soluble cytokine receptors (e.g., the extracellular domain of a TNF-α receptor or a fragment thereof, the extracellular domain of an IL-1β receptor or a fragment thereof, and the extracellular domain of an IL-6 receptor or a fragment thereof), cytokines or fragments thereof (e.g., interleukin (IL)-2, IL-3, IL-4, IL-5, IL-6, IL-7, IL-8, IL-9, IL-10, IL-11, IL-12, IL-15, TNF-α, interferon (IFN)-α, IFN-γ, and GM-CSF), anti-cytokine receptor antibodies (e.g., anti-IFN receptor antibodies, anti-IL-2 receptor antibodies (e.g., Zenapax (Protein Design Labs)), anti-IL-4 receptor antibodies, anti-IL-6 receptor antibodies, anti-IL-10 receptor antibodies, and anti-IL-12 receptor antibodies), anti-cytokine antibodies (e.g., anti-IFN antibodies, anti-TNF-α antibodies, anti-IL-1β antibodies, anti-IL-6 antibodies, anti-IL-8 antibodies (e.g., ABX-IL-8 (Abgenix)), and anti-IL-12 antibodies).

The compound of Formula (1) can be administered or formulated in combination with an agent which inhibits viral enzymes, including but not limited to inhibitors of HCV protease, such as BILN 2061, SCH-503034, ITMN-191 or VX-950; and inhibitors of NS5B polymerase such as NM107 (and its prodrug NM283), R1626, R7078, BILN1941, GSK625433, GILD9128 or HCV-796.

The compound of Formula (1) can be administered or formulated in combination with an agent which inhibits HCV polymerase such as those described in Wu, *Curr Drug Targets Infect Disord.*, 3, 207-19 (2003) or in combination with compounds that inhibit the helicase function of the virus such as those described in Bretner M., et al., *Nucleosides Nucleotides Nucleic Acids.*, 22, 1531 (2003), or with inhibitors of other HCV specific targets such as those described in Zhang X., *IDrugs*, 5(2), 154-8 (2002).

The compound of Formula (1) can be administered or formulated in combination with an agent which inhibits viral replication.

The compound of Formula (1) can be administered or formulated in combination with cytokines. Examples of cytokines include, but are not limited to, interleukin-2 (IL-2), interleukin-3 (IL-3), interleukin-4 (IL-4), interleukin-5 (IL-5), interleukin-6 (IL-6), interleukin-7 (IL-7), interleukin-9 (IL-9), interleukin-10 (IL-10), interleukin-12 (IL-12), interleukin 15 (IL-15), interleukin 18 (IL-18), platelet derived growth factor (PDGF), erythropoietin (Epo), epidermal growth factor (EGF), fibroblast growth factor (FGF), granulocyte macrophage stimulating factor (GM-CSF), granulocyte colony stimulating factor (G-CSF), macrophage colony stimulating factor (M-CSF), prolactin, and interferon (IFN), e.g., IFN-α, and IFN-γ).

The compound of Formula (1) can be administered or formulated in combination with hormones. Examples of hormones include, but are not limited to, luteinizing hormone releasing hormone (LHRH), growth hormone (GH), growth hormone releasing hormone, ACTH, somatostatin, somatotropin, somatomedin, parathyroid hormone, hypothalamic releasing factors, insulin, glucagon, enkephalins, vasopressin, calcitonin, heparin, low molecular weight heparins, heparinoids, synthetic and natural opioids, insulin thyroid stimulating hormones, and endorphins.

The compound of Formula (1) can be administered or formulated in combination with β-interferons which include, but are not limited to, interferon β-1a, interferon β-1b.

The compound of Formula (1) can be administered or formulated in combination with α-interferons which include, but are not limited to, interferon α-1, interferon α-2a (roferon), interferon α-2b, intron, Peg-Intron, Pegasys, consensus interferon (infergen) and albuferon.

The compound of Formula (1) can be administered or formulated in combination with an absorption enhancer, particularly those which target the lymphatic system, including, but not limited to sodium glycocholate; sodium caprate; N-lauryl-β-D-maltopyranoside; EDTA; mixed micelle; and those reported in Muranishi *Crit. Rev. Ther. Drug Carrier Syst.*, 7-1-33, which is hereby incorporated by reference in its entirety. Other known absorption enhancers can also be used.

The compound of Formula (1) can be administered or formulated in combination with an alkylating agent. Examples of alkylating agents include, but are not limited to nitrogen mustards, ethylenimines, methylmelamines, alkyl sulfonates, nitrosoureas, triazenes, mechlorethamine, cyclophosphamide, ifosfamide, melphalan, chlorambucil, hexamethylmelaine, thiotepa, busulfan, carmustine, streptozocin, dacarbazine and temozolomide.

The compound of Formula (1) and the other therapeutics agent can act additively or, more preferably, synergistically. In one embodiment, a composition comprising a compound of the disclosure is administered concurrently with the administration of another therapeutic agent, which can be part of the same composition or in a different composition from that comprising the compounds of the disclosure. In another embodiment, a compound of the disclosure is administered prior to or subsequent to administration of another therapeutic agent. In a separate embodiment, a compound of the disclosure is administered to a patient who has not previously undergone or is not currently undergoing treatment with another therapeutic agent, particularly an antiviral agent.

Methods of Preparation

In another embodiment, the present disclosure provides a method for preparing p-toluene sulfonic acid salt of 5-amino-3-(2'-O-acetyl-3'-deoxy-β-D-ribofuranosyl)-3H-thiazolo[4,5-d]pyrimidin-2-one, shown below as Formula (1)

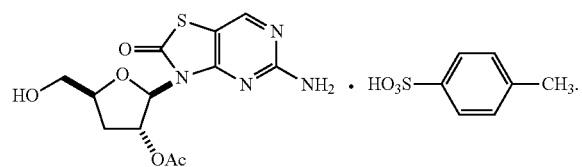

The method is operationally simple, robust and efficient, and can be used for the scalable commercial production of this salt. Furthermore, the method is cost-effective and demonstrates efficient throughput and high overall yield.

In one embodiment, the method of synthesizing p-toluene sulfonic acid salt of 5-amino-3-(2'-O-acetyl-3'-deoxy-β-D-ribofuranosyl)-3H-thiazolo[4,5-d]pyrimidin-2-one (1) comprises the steps of:

(i) coupling 5-amino-3H-thiazolo[4,5-d]pyrimidin-2-one (2) with a deoxyribofuranose (3) to form a compound of Formula (4)

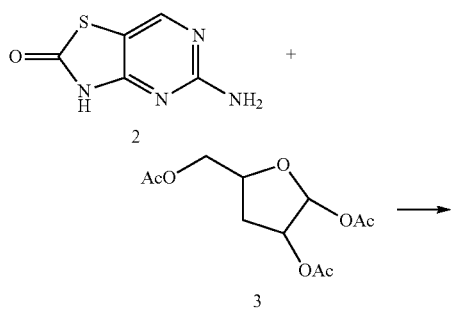

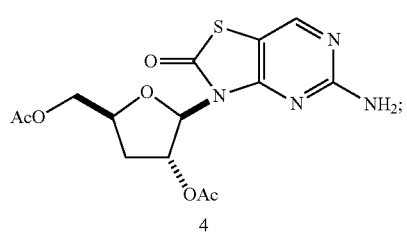

4

(ii) selectively cleaving the 5' acetate on the compound of Formula (4) to form 5-amino-3-(2'-O-acetyl-3'-deoxy-β-D-ribofuranosyl)-3H-thiazolo[4,5-d]pyrimidin-2-one (5)

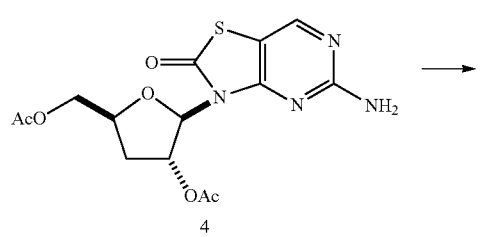

4

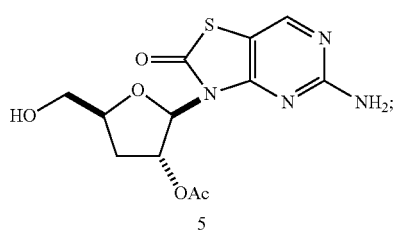

5 and (iii) reacting 5-amino-3-(2'-O-acetyl-3'-deoxy-β-D-ribofuranosyl)-3H-thiazolo[4,5-d]pyrimidin-2-one (5) with p-toluene sulfonic acid to form p-toluene sulfonic acid salt of 5-amino-3-(2'-O-acetyl-3'-deoxy-β-D-ribofuranosyl)-3H-thiazolo[4,5-d]pyrimidin-2-one (1).

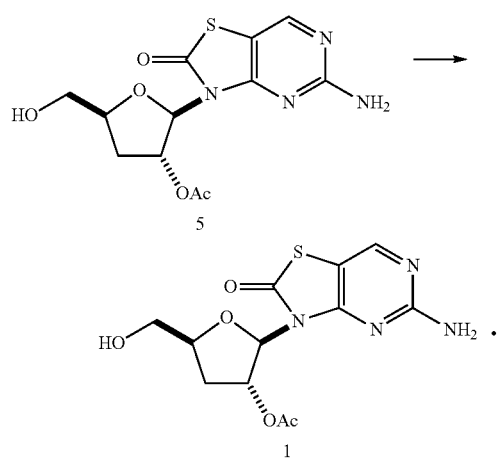

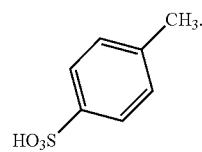

In another embodiment, step (i) comprises coupling 5-amino-3H-thiazolo[4,5-d]pyrimidin-2-one (2) with a deoxyribofuranose of Formula (3B) to form a compound of Formula (4)

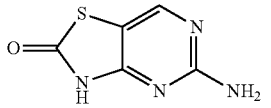
2

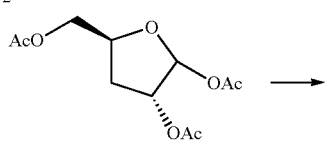
3B

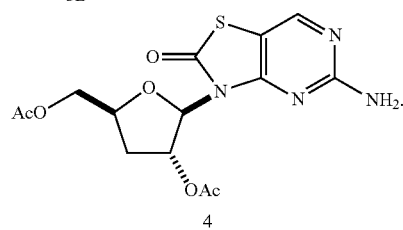
4

The coupling reaction in step (i) can be performed with no solvent in a 'melt' reaction at high temperatures (greater than 130° C.), typically using 1,3bis(4-nitrophenyl) phosphate as an acid catalyst and sometimes under vacuum. Alternatively, the reaction is performed in a solvent such as acetonitrile, toluene, dichloroethane, DMF, methylene chloride and mixtures thereof. The coupling reaction is typically performed in the presence of an acid such as trimethylsilyl triflate ("TMSOTf"), $AlCl_3$, $SnCl_4$ and $TiCl_4$ together with a silating reagent such as N,O-bis(trimethylsilyl)acetamide ("BSA") or trimethylsilyl chloride. Termination of the coupling reaction is then achieved by the addition of water, which acts to quench the excess acid and silating reagent. When TMSOTf and BSA are used, the quenching with water results in the formation of aqueous triflic acid and hexamethyldisiloxane (CAS #107-46-0). The aqueous acid solution serves to hydrolytically remove residual silyl groups from the heterocyclic portion of the compound of Formula (4).

In another embodiment, the coupling reaction of step (i) uses an excess of the 5-amino-3H-thiazolo[4,5-d]pyrimidin-2-one (2) with respect to the deoxyribofuranose (3) based on the reaction stoichiometry. For instance, the 5-amino-3H-thiazolo[4,5-d]pyrimidin-2-one (2) can be in excess from about 5% to about 50%, from about 5% to about 25%, and from about 5% to about 15%. Additionally, the 5-amino-3H-thiazolo[4,5-d]pyrimidin-2-one (2) can be from about 10% in excess of the deoxyribofuranose (3) based on the reaction stoichiometry. The excess 5-amino-3H-thiazolo[4,5-d]pyrimidin-2-one (2) is removed by raising the pH of the completed coupling reaction of step (i) in the presence of an inert solid, which can be coated and removed by filtration. Upon further neutralization (with a base such as sodium bicarbonate), sodium chloride is added to yield a three layer liquid system capable of being phase separated.

The separation of excess 5-amino-3H-thiazolo[4,5-d]pyrimidin-2-one (2) can be difficult. It has been found, however, that raising the pH of the completed reaction mixture in the presence of an inert solid eases the separation method. The pH is raised with a base, such as sodium hydroxide and/or sodium carbonate, in the presence of an inert solid, such as Celite filter aid, to precipitate the excess 5-amino-3H-thiazolo[4,5-d]pyrimidin-2-one (2). The inert solid is coated and then removed by filtration. Upon further neutralization with a base, additional sodium chloride is added to the remaining filtrate to yield the three layer liquid system capable of being phase separated. The least dense (top) layer is clear hexamethyldisiloxane, which may be removed by separating the phases and negating the need for a distillation (a conventional way of removal). The middle phase contains the desired nucleoside (4) and acetonitrile. The most dense (bottom) phase is aqueous based and may be extracted with acetonitrile for additional retrieval of (4) from the reaction mixture. The compound of Formula (4) is now in a state of purity and in a solvent mixture that is adequate for step (ii) without any need of further handling.

In step (ii), the 5' acetate on the compound of Formula (4) is selectively cleaved. This can be accomplished using an enzyme such as *Candida Antarctica*. *Candida Antarctica* is publicly available from Biocatalytics, Inc. Typically the enzyme is covalently solid-supported. A covalently solid-supported enzyme provides for more efficient recycling and demonstrates shorter reaction times. The solution of acetonitrile formed in step (i) containing the compound of Formula (4) is added to a stirred suspension of the supported enzyme and buffer at a pH of about 7. It can also be added to a suspension of supported enzyme in water containing a base, such as sodium bicarbonate or sodium acetate. Alternatively, the solution can be added to anhydrous ethanol and sodium bicarbonate and/or sodium acetate to form a substantially water-free slurry of the supported enzyme. Upon completion of the reaction, the supported enzyme is filtered, washed and stored for later use. Sodium chloride may be added to the filtrate and extracted with isopropyl acetate.

Compounds such 5-amino-3-(2'-O-acetyl-3'-deoxy-β-D-ribofuranosyl)-3H-thiazolo[4,5-d]pyrimidin-2-one (5) are difficult to handle and are often intractable materials. Evaporation of the solvent or precipitation at this stage is an erratic method affording a product state that is suboptimal. The method according to the present disclosure, however, eliminates the need for handing compound (5) and does not require evaporation of solvent or precipitation of product. The 5-amino-3-(2'-O-acetyl-3'-deoxy-β-D-ribofuranosyl)-3H-thiazolo[4,5-d]pyrimidin-2-one (5) is already in a state of purity and in a solvent mixture that is adequate for performing step (iii).

Step (iii) comprises reacting 5-amino-3-(2'-O-acetyl-3'-deoxy-β-D-ribofuranosyl)-3H-thiazolo[4,5-d]pyrimidin-2-one (5) with p-toluene sulfonic acid in a solvent to form p-toluene sulfonic acid salt of 5-amino-3-(2'-O-acetyl-3'-deoxy-β-D-ribofuranosyl)-3H-thiazolo[4,5-d]pyrimidin-2-one (1). The reaction is typically conducted at a temperature from about −20° C. to about 40° C., from about 0° C. to about 30° C., and from about 15° C. to about 30° C. Solvents suitable for the reaction include, for example, ethanol, methanol, n-propanol, isopropanol, n-butanol, isobutanol, ethyl acetate, acetonitrile, isopropyl acetate, THF and mixtures thereof. For example, the solvent may comprise a mixture of isopropyl acetate and acetonitrile. In one embodiment, the mixture of isopropyl acetate and acetonitrile is generated in step (ii) and the method further comprises adding ethanol. Typically, the amount of sulfonic acid used in step (iii) is about an equimolar amount to about a 10% molar excess amount based on the reaction stoichiometry.

The reaction in step (iii) is carried out in any concentration of the reactants. For instance, the reactant concentration can vary from about 1 millimolar to about 1000 millimolar. In addition, the concentration ranges from about 50 millimolar to about 500 millimolar or from about 100 millimolar to about 250 millimolar.

A solution of 5-amino-3-(2'-O-acetyl-3'-deoxy-β-D-ribofuranosyl)-3H-thiazolo[4,5-d]pyrimidin-2-one (5) is reacted with a solution of p-toluene sulfonic acid. The solutions are mixed over a period from about 5 minutes to about 2 hours, or from about 5 minutes to about 1 hour. Additionally, the p-toluene sulfonic acid solution may be added to the reaction mixture from which the compound of Formula (1) is synthesized as described in U.S. Application Publication No. 2006/0160830 (Ser. No. 11/304,691), which is incorporated herein by reference in its entirety.

The reaction of step (iii) is conducted at a temperature from about −20° C. to about 40° C., from about 0° C. to about 30° C., and from about 15° C. to about 30° C. Solvents suitable for the reaction include ethanol, methanol, n-propanol, isopropanol, n-butanol, isobutanol, ethyl acetate, acetonitrile, isopropyl acetate, THF and mixtures thereof. In one embodiment, the mixture comprises isopropyl acetate and acetonitrile, which is generated in step (ii), and the method further comprises adding ethanol to this mixture. Typically, the amount of sulfonic acid used in step (iii) is about an equimolar amount to about a 25% molar excess amount or about an equimolar amount to about a 10% molar excess amount based on the reaction stoichiometry.

Upon mixing the solutions of 5-amino-3-(2'-O-acetyl-3'-deoxy-β-D-ribofuranosyl)-3H-thiazolo[4,5-d]pyrimidin-2-one (5) with a solution of p-toluene sulfonic acid, the p-toluene sulfonic acid salt of 5-amino-3-(2'-O-acetyl-3'-deoxy-β-D-ribofuranosyl)-3H-thiazolo[4,5-d]pyrimidin-2-one (1) precipitates or crystallizes The reaction product can then be isolated by filtration, washing and drying. The reaction product may also be isolated by evaporating the solvent from the reaction mixture, precipitating or crystallizing the product from an alternate solvent system, or isolated by cooling the reaction mixture to precipitate or crystallize the product. The isolated product of p-toluene sulfonic acid salt of 5-amino-3-(2'-O-acetyl-3'-deoxy-β-D-ribofuranosyl)-3H-thiazolo[4,5-d]pyrimidin-2-one (1) is typically washed, and then dried at a temperature from about 40° C. to about 70° C. or from about 50° C. to about 60° C. The drying method may be carried out at atmospheric pressure or under reduced pressure (vacuum). The reduced pressure may range from about 0.1 to about 10 inches of mercury.

The method disclosed herein can further comprise the step of isolating the p-toluene sulfonic acid salt of 5-amino-3-(2'-O-acetyl-3'-deoxy-β-D-ribofuranosyl)-3H-thiazolo[4,5-d]pyrimidin-2-one (1) wherein the purity of the isolated salt is at least 95%, 96%, 97%, 98%, 99%, 99.5%, 99.6%, 99.7%, 99.8%, or 99.9% pure.

The present disclosure also provides method for preparing compounds of Formula (3) and Formula (3B). The following schematics illustrate these methods.

In a first reaction sequence (Scheme 1), a compound of Formula (6) is sulfonated with a sulfonating agent in the presence of a base to form a sulfonyl substituted compound of Formula (7). The reaction sequence (Scheme 1) is as follows:

Scheme 1

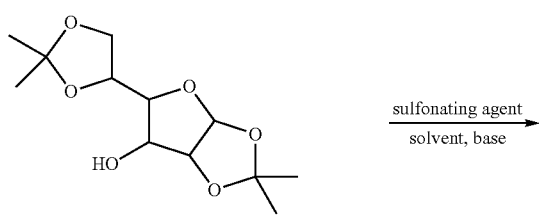

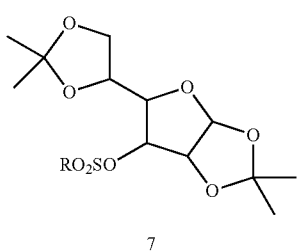

The sulfonating agent, base and solvent are not limited provided they can effect the chemical reaction described in Scheme 1. The R group in Scheme 1 can be an optionally substituted alkyl or aryl group.

Non-limiting sulfonating agents include alkyl sulfonic anhydride, an alkyl sulfonic halide, an aromatic sulfonic anhydride, an aromatic sulfonic halide and mixtures thereof. Sulfonating agents include triflic anhydride, tosylchloride, methane sulfonic anhydride, methane sulfonic halide, benzensulfonic halide, substituted benzensulfonic halide, benzensulfonic anhydride, substituted benzensulfonic anhydride and mixtures thereof.

The base used in Scheme 1 is not limited and can be an organic or inorganic base, such as triethylamine, diisopropylethylamine, imidazole or pyridine.

The solvent used in reaction Scheme 1 is not limited. A halogen containing solvent such as dichloromethane, dichloroethane and mixtures thereof can be used. In general, non-protic solvents such as tetrahydrofuran or acetonitrile may be used.

The reaction sequence in Scheme 1 is conducted at a temperature of about −40° C. to about 25° C. Additionally, the reaction may be conducted at a temperature of about −20° C. to about 0° C.

In a next sequence (Scheme 2), the sulfonyl substituted compound of Formula (7) formed in reaction Scheme 1 is reduced with a reducing agent to form a compound of Formula (8). The reaction sequence (Scheme 2) is as follows:

Scheme 2

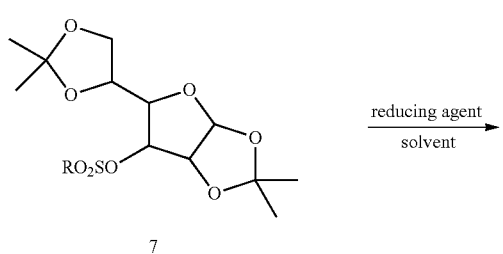

-continued

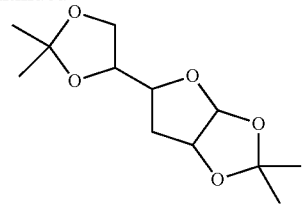

The reducing agent used in reaction Scheme 2 is not limited provided the reducing agent can effect the required reduction reaction. The reducing agent may be a borohydride compound. The borohydride compound can be a tetraalkylammonium borohydride, tetrabutyl ammonium borohydride, sodium borohydride, sodium cyanoborohydride, lithium borohydride, potassium borohydride, magnesium borohydride, calcium borohydride, sodium triacetoxyborohydride and mixtures thereof.

The solvent used in reaction Scheme 2 is not limited. Aromatic solvents or mixtures of aromatic solvents may be used. Solvents such as toluene, benzene, xylene, other substituted benzene compounds and mixtures thereof may be used. In addition, non-protic solvents such as dioxane, dichloroethane, tetrahydrofuran and mixtures thereof may be used.

The reaction sequence of Scheme 2 is conducted at a temperature of about 25° C. to about 100° C. In addition, the temperature may be conducted at a temperature of about 60° C. to about 80° C.

In a next reaction sequence (Scheme 3), the compound of Formula (8) formed in reaction Scheme 2 is hydrolyzed with water in the presence of an acid to form a compound of Formula (9). The reaction sequence (Scheme 3) is as follows:

Scheme 3

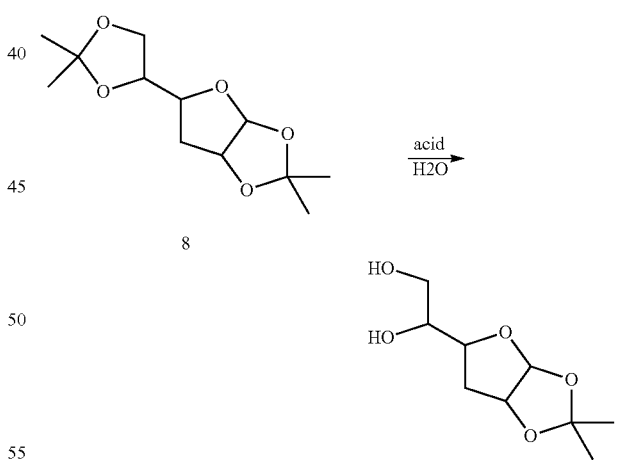

The acid used in reaction Scheme 3 is not limited and either inorganic or organic acids can be used. The reaction may be conducted in an aqueous solvent. The reaction may also be conducted with a 50% aqueous acetic solution or an aqueous HCl solution.

The reaction sequence of Scheme 3 is conducted at a temperature of about 0° C. to about 50° C. The reaction sequence of Scheme 3 may also be conducted at a temperature of about 20° C. to about 30° C.

In a next reaction sequence (Scheme 4), the compound of Formula (9) formed in reaction Scheme 3 is oxidized with an oxidizing agent then reduced with a reducing agent to form a compound of Formula (10). The reaction sequence (Scheme 4) is as follows:

Scheme 4

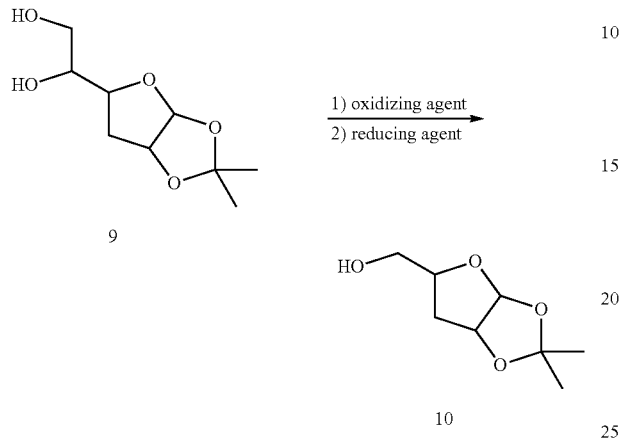

The oxidizing agent used in reaction Scheme 4 is not limited provided the oxidizing agent can effect the require oxidizing reaction. Oxidizing agents include sodium periodate, lead acetate and mixtures thereof.

The reducing agent used in reaction Scheme 4 is not limited and includes the reducing agents listed above used in reaction Scheme 2.

The solvent used in reaction Scheme 4 is not limited. Solvents include methanol, methylene chloride, a combination of methylene chloride and methanol or a combination of methanol and water.

The reaction sequence of Scheme 4 is conducted at a temperature of about 0° C. to about 50° C. In addition, the reaction sequence of Scheme 4 may be conducted at a temperature at about 20° C. to about 30° C.

In a final reaction sequence (Scheme 5), the compound of Formula (10) formed in reaction Scheme 4 is acetylated with an acetylating agent such as acetic ahydride or acetic chloride in the presence of an acid catalyst to form the compound of Formula (3). The reaction sequence (Scheme 5) is as follows:

Scheme 5

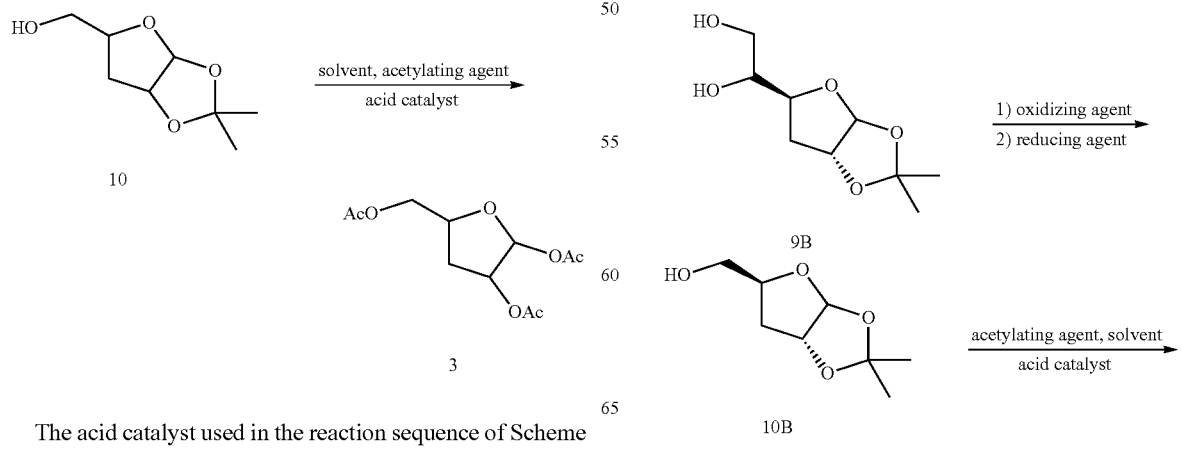

The acid catalyst used in the reaction sequence of Scheme 5 is not limited and includes an inorganic acid, an organic acid or both an inorganic acid and an organic acid. Acids include nitric acid, hydrochloric acid, sulfuric acid, sulfurous acid, trifloroacetic acid, alkyl sulfonic acid, arylsulfonic acid and immobilized forms and mixtures thereof.

The reaction sequence of Scheme 5 is typically conducted in an organic solvent which contains the acid catalysts listed above. The solvent can also be acetic acid.

The reaction sequence of Scheme 5 is conducted at a temperature of about 0° C. to about 50° C. In addition, the reaction sequence of Scheme 5 may be conducted at a temperature of about 20° C. to about 30° C.

In a further embodiment of the disclosure, the general reaction scheme disclosed above (Schemes 1-5) can be conducted with a glucofuranose compound starting reactant of Formula (6B) to give the acetyl-deoxy-xylofuranose compound of Formula (3B) as shown in reaction Scheme 6 as follows:

Scheme 6

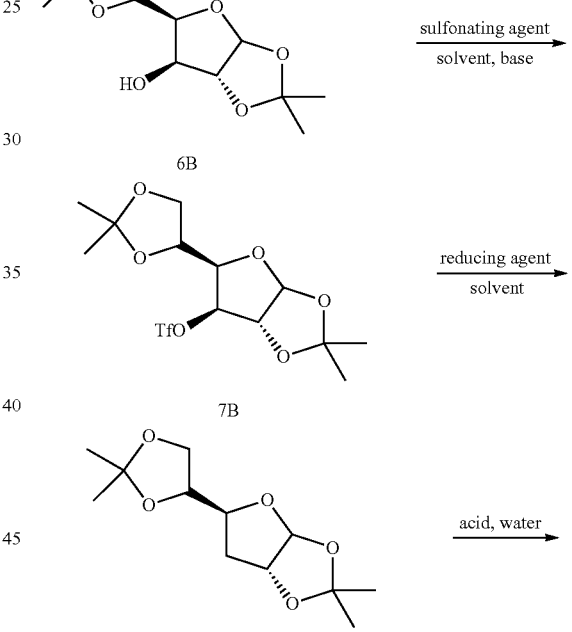

-continued

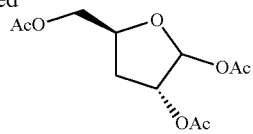

3B

The reagents and reaction conditions described above for Schemes 1-5 may be used in reaction Scheme 6.

In a further embodiment of the disclosure, the general reaction scheme disclosed above (Schemes 1-5) can be conducted with an allofuranose compound starting reactant of Formula (6C) to give the acetyl-deoxy-xylofuranose compound of Formula (3B) as shown in reaction Scheme 7 as follows:

-continued

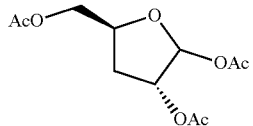

3B

The reagents and reaction conditions described above for Schemes 1-5 may be used in reaction Scheme 7.

The disclosure also includes an embodiment where a mixture of compounds of Formula (6B) and (6C) are used as starting materials to form the final product of Formula (3B) using the general overall reaction scheme outlined in Schemes 1-5.

The acetyl-deoxy-xylofuranose compound, 1,2,5-tri-O-acetyl-3-deoxy-D-xylofuranose (3B), is prepared according to reaction Scheme 8 as follows:

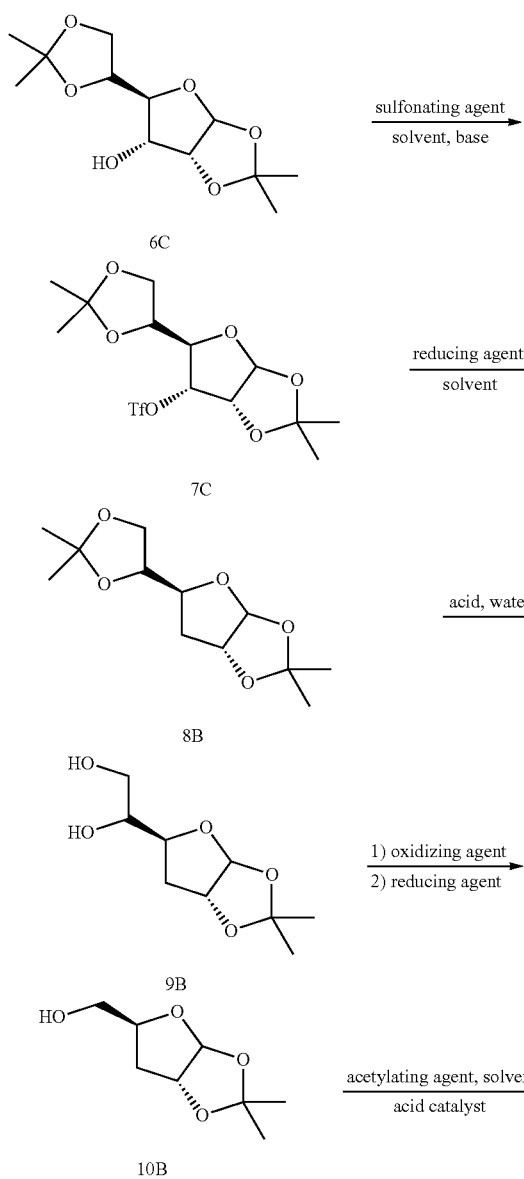

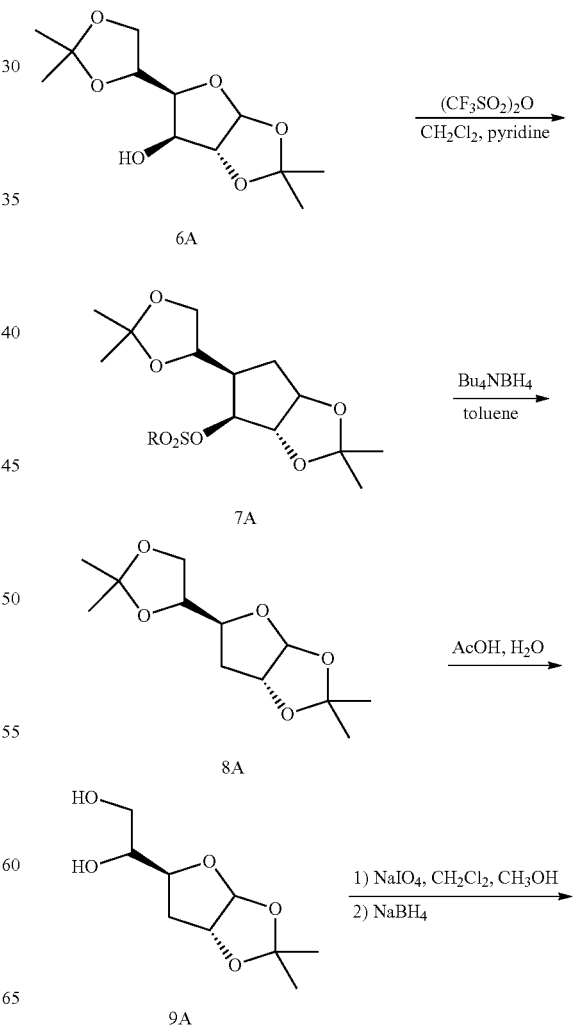

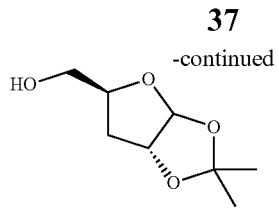

10A

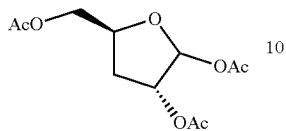

3B

The reagents and reaction conditions described above for Schemes 1-5 may be used in reaction Scheme 8.

An additional embodiment of the disclosure includes a method of reducing a sulfonyl substituted compound of Formula (7)

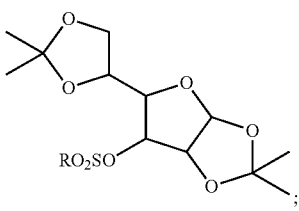

7 with a reducing agent to form a compound of Formula (8)

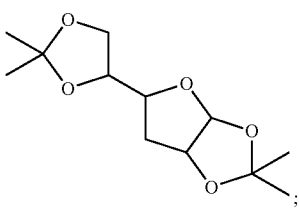

8 wherein R represents an optionally substituted alkyl or aryl group.

In one particular embodiment of the disclosure, R is $CF_3$, $CH_3$, or —$C_6H_4CH_3$. The compound of Formula (7) may be the glucofuranose isomer of Formula (7B) or the allofuranose isomer of Formula (7C) given above or a mixture of compounds of Formula (7B) and (7C)

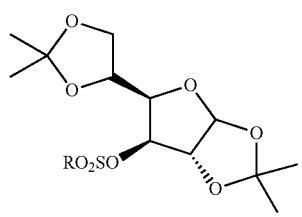

7B

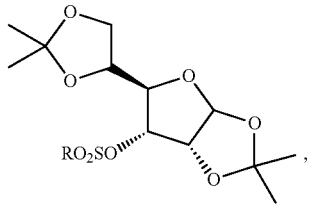

7C or a mixture of both.

The reducing agent may be a borohydride compound. The borohydride compound can be a tetraalkylammonium borohydride, tetrabutyl ammonium borohydride, sodium borohydride, sodium cyanoborohydride, lithium borohydride, potassium borohydride, magnesium borohydride, calcium borohydride, sodium triacetoxyborohydride and mixtures thereof.

EXAMPLES

The following examples are for illustrative purposes only and are not intended to limit the scope of the claims.

In the synthetic schemes described below, unless otherwise indicated all temperatures are set forth in degrees Celsius and all parts and percentages are by weight.

Reagents were purchased from commercial suppliers such as Aldrich Chemical Company or Lancaster Synthesis Ltd. and were used without further purification unless otherwise indicated. All solvents were purchased from commercial suppliers such as Aldrich, EMD Chemicals or Fisher and used as received.

The reactions set forth below were done generally under a positive pressure of nitrogen or argon at an ambient temperature (unless otherwise stated) in anhydrous solvents, and the reaction flasks were fitted with rubber septa for the introduction of substrates and reagents via syringe. Glassware was oven dried and/or heat dried.

The reactions were assayed by TLC and/or analyzed by LC-MS and terminated as judged by the consumption of starting material. Analytical thin layer chromatography (TLC) was performed on glass-plates precoated with silica gel 60 $F_{254}$ 0.25 mm plates (EMD Chemicals), and visualized with UV light (254 nm) and/or iodine on silica gel and/or heating with TLC stains such as ethanolic phosphomolybdic acid, ninhydrin solution, potassium permanganate solution or ceric sulfate solution. Preparative thin layer chromatography (prepTLC) was performed on glass-plates precoated with silica gel 60 $F_{254}$ 0.5 mm plates (20×20 cm, from Thomson Instrument Company) and visualized with UV light (254 nm).

$^1$H-NMR spectra and $^{13}$C-NMR were recorded on a Varian Mercury-VX400 instrument operating at 400 MHz. NMR spectra were obtained as $CDCl_3$ solutions (reported in ppm), using chloroform as the reference standard (7.27 ppm for the proton and 77.00 ppm for carbon), $CD_3OD$ (3.4 and 4.8 ppm for the protons and 49.3 ppm for carbon), DMSO-$d_6$ (2.49 ppm for proton), or internally tetramethylsilane (0.00 ppm) when appropriate. Other NMR solvents were used as needed. When peak multiplicities are reported, the following abbreviations are used: s (singlet), d (doublet), t (triplet), q (quartet), m (multiplet), br (broadened), bs (broad singlet), dd (doublet of doublets), dt (doublet of triplets). Coupling constants, when given, are reported in Hertz (Hz).

Infrared (IR) spectra were recorded on an ATR FT-IR Spectrometer as neat oils or solids, and when given are reported in wave numbers (cm$^{-1}$). Mass spectra reported are (+)-ES or APCI (+) LC/MS conducted by the Analytical Chemistry Department of Anadys Pharmaceuticals, Inc. Elemental analyses were conducted by the Atlantic Microlab, Inc. in Norcross, Ga. Melting points (mp) were determined on an open capillary apparatus, and are uncorrected.

The described synthetic pathways and experimental procedures may utilize many common chemical abbreviations, 2,2-DMP (2,2-dimethoxypropane), Ac (acetyl), ACN (acetonitrile), Bn (benzyl), BOC (tert-butoxycarbonyl), Bz (benzoyl), DBU (1,8-diazabicyclo[5,4,0]undec-7-ene, DCC(N,N'-dicyclohexylcarbodiimide), DCE (1,2-dichloroethane), DCM (dichloromethane), DEAD (diethylazodicarboxylate), DIEA (diisopropylethylamine), DMA (N,N-dimethylacetamide), DMAP (4-(N,N-dimethylamino)pyridine), DMF (N,N-dimethylformamide), DMSO (dimethyl sulfoxide), EDC (1-β-dimethylaminopropyl)-3-ethylcarbodiimide hydrochloride), Et (ethyl), EtOAc (ethyl acetate), EtOH (ethanol), HATU (O-(7-azabenzotriazol-1-yl)-1,1,3,3-tetramethyluronium hexafluorophosphate), HBTU (O-benzotriazol-1-yl-N,N,N',N'-tetramethyluronium hexafluorophosphate), HF (hydrogen fluoride), HOBT (1-hydroxybenzotriazole hydrate), HPLC (high pressure liquid chromatography), IPA (isopropyl alcohol), KO$^t$Bu (potassium tert-butoxide), LDA (lithium diisopropylamide), MCPBA (3-chloroperoxybenzoic acid), Me (methyl), MeCN (acetonitrile), MeOH (methanol), NaH (sodium hydride), NaOAc (sodium acetate), NaOEt (sodium ethoxide), Phe (phenylalanine), PPTS (pyridinium p-toluenesulfonate), PS (polymer supported), Py (pyridine), pyBOP (benzotriazol-1-yloxy)tripyrrolidinophosphonium hexafluorophosphate), TEA (triethylamine), TFA (trifluoroacetic acid), TFAA (trifluoroacetic anhydride), THF (tetrahydrofuran), TLC (thin layer chromatography), Tol (toluoyl), Val (valine), and the like.

Example 1

Synthesis of p-toluene sulfonic acid salt of 5-amino-3-(2'-O-acetyl-3'-deoxy-β-D-ribofuranosyl)-3H-thiazolor-[4,5-]pyrimidine-2-one)

Step (i)—Coupling Reaction

A three necked flask equipped with a temperature probe, condenser and nitrogen inlet is charged with 5-amino-3H-thiazolo[4,5-d]pyrimidine-2-one (2) [prepared according to the method of Wolfe et al. *J. Org. Chem.* 1997, 62, 1754-1759] (22 g, 130.9 mmol) and acetonitrile (198 mL). While stirring under a slow purge of nitrogen BSA (79.86 mL, 327.8 mmol) is added via a funnel and this mixture is warmed to 40° C. for 90 minutes under an atmosphere of nitrogen. The dark, homogeneous solution is cooled to 5° C. using an ice bath and 1,2,5-tri-O-acetyl-β-D-ribofuranose (3) (35.42 g, 111.32 mmol) in 66 mL of acetonitrile is added. While stirring under nitrogen TMSOTf (23.54 mL, 130.9 mmol) is added via a pipette, causing an exothermic reaction to 15° C. This mixture is then warmed to 75° C. and maintained at this temperature for ten hours and then cooled, first to ambient temperature, and then to 15° C. using a cool water bath. Water is added to the reaction in one mL portions, allowing the exothermic reaction to peak between each addition. After six additions the addition of an additional one mL portion is not exothermic, then 38 mL of water is added via a funnel and this mixture is stirred for 15 minutes at ambient temperature. Celite (44 g) is added to the stirring reaction followed by sodium hydroxide (15.7 g 50% NaOH, 196.35 mmol) in 22 mL of water over about 30 seconds. Stir at ambient temperature for 90 minutes and filter the reaction. To the stirring filtrate is added sodium bicarbonate (16.5 g, 196.35 mmol) dissolved in 200 mL of water. When the bubbling stops 50 g of sodium chloride is added as a solid and the mixture is stirred until all of the solid is dissolved. This mixture is transferred to a separatory funnel and the resulting three liquid phase system is split. The densest phase is extracted once with 50 mL of acetonitrile and this is combined with the middle phase of the original split. To this is added 11 g of Celite while stirring, after 5 minutes the mixture is filtered. The filtrate contains the desired coupled product (4); its identity and purity is determined by HPLC using the known material.

Step (ii)—Enzymatic Hydrolysis

To a solution of sodium bicarbonate (9.34 g, 111.32 mmol, equivalent to sugar (3) in step (i)), dissolved in 278 mL of water is added the damp, pre-washed covalently supported lipase [Washing Procedure: A 23.21 g sample of dry, covalently bound *Candida antarctica*, type B (Biocatalytics catalog number IMB-111) was suspended in a 1:1 solution of acetonitrile and water, stirred for 4 hours, filtered and washed with 60 mL of acetonitrile-water (1:1)]. To this stirring solution is added the acetonitrile solution of (4) generated in step (i). This suspension is stirred for 36 hours, the catalyst is filtered, washed with acetonitrile-water (1:1) and stored at 0° C. for later reuse. The filtrate is extracted with 222 mL of isopropyl acetate, the aqueous phase was stirred with 30 g of sodium chloride until all of the solid is dissolved, and then extracted two more times with 111 mL portions of isopropyl acetate. The organic portions were combined, dried with MgSO$_4$, stirred with 2.5 g of Norit 211 for 90 minutes and filtered through Celite filter aid. The filtrate contains the desired alcohol (5); its identity and purity is determined by HPLC using the known material as a standard.

Step (iii)—Salt Formation with p-Toluene Sulfonic Acid

The filtrate from step (ii) that contains (5) dissolved in isopropyl acetate and acetonitrile is diluted with 100 mL of 200 proof ethanol. While stirring, p-toluene sulfonic acid hydrate (15.89 g, 83.49 mmol) in 50 mL of 200 proof ethanol is added dropwise over 30 minutes. An off white solid crystallizes from the reaction mixture. After stirring 16 hours the solid is collected by filtration, washed twice with 100 mL portions of isopropyl acetate, and once with 50 mL of 200 proof ethanol. The solid is dried in a vacuum oven to yield 30.55 g of p-toluene sulfonic acid salt of 5-amino-3-(2'-O-acetyl-3'-deoxy-β-D-ribofuranosyl)-3H-thiazolo[4,5]pyrimidine-2-one with >98% purity by HPLC.

Example 2

Synthesis of p-toluene sulfonic acid salt of 5-amino-3-(2'-O-acetyl-3'-deoxy-β-D-ribofuranosyl)-3H-thiazolor-4,5-ipyrimidine-2-one) without adding water to the enzymatic hydrolysis of step (ii)

Step (i)—Coupling Reaction

A three necked flask equipped with a temperature probe, condenser and nitrogen inlet is charged with 5-amino-3H-thiazolo[4,5-d]pyrimidine-2-one (2) (22 g, 130.9 mmol) and acetonitrile (198 mL). While stirring under a slow purge of nitrogen BSA (79.86 mL, 327.8 mmol) is added via a funnel and this mixture is warmed to 40° C. for 90 minutes under an atmosphere of nitrogen. The dark, homogeneous solution is cooled to 5° C. using an ice bath and 1,2,5-tri-O-acetyl-β-D-ribofuranose (3) (35.42 g, 111.32 mmol) in 66 mL of acetonitrile is added. While stirring under nitrogen TMSOTf (23.54 mL, 130.9 mmol) is added via a pipette, causing an exothermic reaction to 15° C. This mixture is then warmed to 75° C. and maintained at this temperature for ten hours and then cooled, first to ambient temperature, and then to 15° C. using a cool water bath. Water is added to the reaction in one mL portions, allowing the exothermic reaction to peak between each addition. After six additions the addition of an additional one mL portion is not exothermic, then 38 mL of water is added via a funnel and this mixture is stirred for 15 minutes at ambient temperature. Celite (44 g) is added to the stirring reaction followed by sodium hydroxide (15.7 g 50% NaOH, 196.35 mmol) in 22 mL of water over about 30 seconds. Stir at ambient temperature for 90 minutes and filter the reaction. To the stirring filtrate is added sodium bicarbonate (16.5 g, 196.35 mmol) dissolved in 200 mL of water. When the bubbling stops 50 g of sodium chloride is added as a solid and the mixture is stirred until all of the solid is dissolved. This mixture is transferred to a separatory funnel and the resulting three liquid phase system is split. The densest phase is extracted once with 50 mL of acetonitrile and this is combined with the middle phase of the original split. To this is added 11 g of Celite while stirring, after 5 minutes the mixture is filtered. The filtrate contains the desired coupled product (4); its identity and purity is determined by HPLC using the known material.

Step (ii), Enzymatic Hydrolysis without Adding any Water

To a 500 mL round bottom flask is added 15.0 g of immobilized *Candida antarctica* (Novozyme 435, Biocatalytics catalog number IMB-102), followed by dry ethanol (60 mL). To this is added the acetonitrile solution of (4) generated in step (i) and the flask is sealed from the atmosphere and stirred at ambient temperature. After 72 hours 17.5 g of Celite 545 was added and stirred for 10 minutes and then the solids were filtered and washed with 80 mL of ethanol. The filtrate contains the desired alcohol (5); its identity and purity is determined by HPLC using the known material as a standard.

Step (iii)—Salt Formation with p-Toluene Sulfonic Acid

The filtrate from step (ii) that contains (5) dissolved in ethanol and acetonitrile is diluted with 100 mL of 200 proof ethanol. While stirring, p-toluene sulfonic acid hydrate (15.89 g, 83.49 mmol) in 50 mL of 200 proof ethanol is added dropwise over 30 minutes. An off white solid crystallizes from the reaction mixture. After stirring 16 hours the solid is collected by filtration, washed twice with 100 mL portions of isopropyl acetate, and once with 50 mL of 200 proof ethanol. The solid is dried in a vacuum oven to yield 30.55 g of p-toluene sulfonic acid salt of 5-amino-3-(2'-O-acetyl-3'-deoxy-β-D-ribofuranosyl)-3H-thiazolo[4,5]pyrimidine-2-one with >98% purity by HPLC.

Example 3

Scaled-up Synthesis of p-toluene sulfonic acid salt of 5-amino-3-(2'-O-acetyl-3'-deoxy-(3-D-ribofuranosyl)-3H-thiazolo[4,5-d]pyrimidin-2-one Step (i)—Coupling Reaction A reactor equipped with a temperature probe, condenser and nitrogen inlet is charged with 5-amino-3H-thiazolo[4,5-d]pyrimidine-2-one (2) (1.45 kg, 8.6 mol) and acetonitrile (1.29 L). While stirring under a slow purge of nitrogen BSA (5.23 L, 21.5 mol) is added via a funnel and this mixture is warmed to 40° C. for 90 minutes under an atmosphere of nitrogen. The dark, homogeneous solution is cooled to 5° C. and 1,2,5-tri-O-acetyl-beta-D-ribofuranose (3) (2.33 kg, 7.32 mol) in 4.3 L of acetonitrile is added. While stirring under nitrogen TMSOTf (1.54 L, 8.6 mol) is added dropwise causing an exothermic reaction to 15° C. This mixture is then warmed to 75° C. and maintained at this temperature for ten hours and then cooled, first to ambient temperature, and then to 15° C.

Water is added to the reaction in 100 mL portions, allowing the exothermic reaction to peak between each addition. When a final 100 mL portion of water no longer causes an exothermic reaction 1.9 L of water is added via a funnel and this mixture is stirred for 15 minutes at ambient temperature. Celite (2.47 kg) is added to the stirring reaction followed by sodium hydroxide (516.8 g, 12.92 mol) in 14.5 L of water. Stir at ambient temperature for 90 minutes and filter the reaction. To the stirring filtrate is added sodium bicarbonate 1.08 kg, 12.92 mol) dissolved in 14.5 L of water. When the bubbling stops 3.3 kg of sodium chloride is added as a solid and the mixture is stirred until all of the solid is dissolved. The resulting three liquid phase system is split. The most dense phase is extracted once with 3.3 L of acetonitrile and this is combined with the middle phase of the original split. These combined phases contain the desired coupled product (4); its identity and purity is determined by HPLC using the known material as a standard.

Step (ii)—Enzymatic Hydrolysis

To a solution of sodium bicarbonate (615 g, 7.32 mol, equivalent to sugar (3) in step (i)), dissolved in 21.5 L of water is added the dry, covalently bound *Candida antarctica*, type B (1.59 kg, Biocatalytics catalog number IMB-111). To this stirring solution is added the acetonitrile solution of (4) generated in step (i). This suspension is stirred for 36 hours, the catalyst is filtered, washed with acetonitrile-water (1:1) and stored at 0° C. for later reuse. The filtrate is extracted with one 17.5 L portion of isopropyl acetate, the aqueous phase was stirred with 3.3 kg of sodium chloride until all of the solid is dissolved, and then extracted two more times with 9 L portions of isopropyl acetate. The organic portions were combined, dried with $MgSO_4$, stirred with 117 g of Norit 211 for 90 minutes and filtered through Celite filter aid. The filtrate contains the desired alcohol (5); its identity and purity is determined by HPLC using the known material as a standard.

Step (iii)—Salt Formation with p-Toluene Sulfonic Acid

The filtrate from step (ii) that contains (5) dissolved in isopropyl acetate and acetonitrile is diluted with 5.5 L of 200 proof ethanol. While stirring, p-toluene sulfonic acid hydrate (1.04 kg, 5.49 mol) in 3.3 L of 200 proof ethanol is added dropwise over 30 minutes. An off white solid crystallizes from the reaction mixture. After stirring 16 hours the solid is collected by filtration, washed twice with 7.5 L portions of isopropyl acetate, and once with 3.5 L of 200 proof ethanol. The solid is dried in a vacuum oven to yield 2.38 kg of p-toluene sulfonic acid salt of 5-amino-3-(2'-O-acetyl-3'-deoxy-beta-D-ribofuranosyl)-3H-thiazolo[4,5]pyrimidine-2-one with >98% purity by HPLC.

Example 4

Crystallizing p-toluene sulfonic acid salt of 5-amino-3-(2'-O-acetyl-3'-deoxy-β-D-ribofuranosyl)-3H-thiazolo[4,5-d]pyrimidin-2-one 5-amino-3-(2'-O-acetyl-3'-deoxy-β-D-ribofuranosyl)-3H-thiazolo[4,5-d]pyrimidin-2-one [50.0 g, (43.85 g, 134 mmol effective based on CoA)] is added to a 2-L, 3-neck flask. Absolute ethanol (840 mL) is added, and the mixture is stirred at ambient temperature for ~10 min to give a pale yellow solution. p-Toluene sulfonic acid (pTsOH) (26.2 g, 138 mmol) is added to a separate flask and is dissolved in absolute ethanol (220 mL) at ambient temperature. The p-TsOH/ethanol solution is added to an addition funnel, and is then added dropwise to the stirring solution of Formula (5) over a period of 40 min at ambient temperature. The flask used for preparation of the p-TsOH/ethanol solution and the addition funnel are rinsed with absolute ethanol (3×20 mL), with each rinse directed into the reaction suspension. The reaction is stirred under $N_2$ at ambient temperature overnight (18 h), and is then vacuum-filtered using a Buchner funnel and Whatman #1 paper. The remaining solids in the flask were transferred to the filter with absolute ethanol (2×50 mL), and the filter cake is then washed with absolute ethanol (4×150 mL). After briefly drying the filter cake on the filter with suction, the damp white solid is dried in a vacuum oven at 50-55° C. with 28-29 inches of vacuum and a $N_2$ bleed for 54 h. After cooling to ambient temperature under vacuum, 62.9 g (93.8% yield) of Formula (1) is obtained as white crystals with 99.1% HPLC purity.

Isolation of a second crop of Formula (1): The combined supernatant and washes from above are concentrated to a volume of 470 mL on a rotary evaporator (45-50° C. bath, 28-29 inches of vacuum). The resulting solution, containing crystallizing particles, is cooled to ambient temperature with stirring. Within 5 min., a crystal suspension is formed. The suspension is stirred at ambient temperature for ~48 h, and is then vacuum-filtered using a Buchner funnel and Whatman #1 paper. The filter cake is washed with absolute ethanol (4×6 mL), and the solid is then dried in a vacuum oven at 50-55° C. with 28-29 inches of vacuum and a $N_2$ bleed for 48 h. After cooling to ambient temperature under vacuum, 2.8 g (4.2% yield) of Formula (1) is obtained as a second crop of Formula (1) with 96% HPLC purity.

Example 5

1,2:5,6-Di-O-isopropylidene-3-O-trifluoromethansulfonyl-α-D-glucofuranose (7a)

Triflic anhydride (10.9 mL, 64.9 mmol) was added dropwise to a −20 to −10° C. stirring solution of 1,2:5,6-Di-O-isopropylidene-α-D-glucofuranose (13.0 g, 50.0 mmol), pyridine (10.0 mL, 124 mmol), and $CH_2Cl_2$ (300 mL) while keeping the internal temperature below −10° C. The resulting solution was stirred between −10 and 0° C. while monitoring by TLC for disappearance of starting material (~1 h required). The reaction solution was washed with $H_2O$ (2×100 mL) followed by saturated aqueous NaCl (50 mL). The organic phase was dried over $Na_2SO_4$ and was then filtered. The filtrate was concentrated to dryness on a rotary evaporator (~30° C.) to give 20.4 g (100%) of 1,2:5,6-di-O-isopropylidene-3-O-trifluoromethansulfonyl-α-D-glucofuranose (7a) as a white waxy solid. This material was carried on directly to the next step without further purification. $^1$H NMR (400 MHz, $CDCl_3$) δ 5.99 (d, 1H), 5.26 (d, 1H), 4.76 (d, 1H), 4.14-4.25 (m, 3H), 3.96-3.99 (dd, 1H), 1.53 (s, 3H), 1.44 (s, 3H), 1.35 (s, 3H), 1.34 (s, 3H).

Example 6

3-Deoxy-1,2:5,6-di-O-isopropylidene-α-D-glucofuranose (8B)

A mixture of 1,2:5,6-di-O-isopropylidene-3-O-trifluoromethansulfonyl-α-D-glucofuranose (7a) (20.4 g, 52.0 mmol) and n-$Bu_4NBH_4$ (40.0 g, 155 mmol) in toluene (500 mL) was degassed by bubbling with $N_2$ for 20 min. The mixture was heated at 80° C. under $N_2$ while monitoring by TLC for disappearance of starting material (~6 h required). The reaction solution was cooled to ambient temperature and $H_2O$ (200 mL) was then carefully added. The resulting mixture was stirred at ambient temperature until no more $H_2$ evolved. The two phases were separated, and the organic phase was then sequentially washed with $H_2O$ (2×200 mL) and saturated aqueous NaCl (100 mL). Concentration of the organic phase on a rotary evaporator (40-50° C.) gave 9.5 g (78%) of 3-deoxy-1,2:5,6-di-O-isopropylidene-α-D-glucofuranose (8a) as a clear oil. This material was used in the next step without further purification (note 5): $^1$H NMR (400 MHz, $CDCl_3$) δ 5.8 (d, 1H), 4.75 (t, 1H), 4.08-4.19 (m, 3H), 3.79-3.85 (m, 1H), 2.17-2.21 (dd, 1H), 1.73-1.80 (m, 1H), 1.51 (s, 3H), 1.43 (s, 3H), 1.36 (s, 3H), 1.32 (s, 3H).

Example 7

3-Deoxy-1,2-O-isopropylidene-α-D-glucofuranose (9a)

3-Deoxy-1,2:5,6-di-O-isopropylidene-α-D-glucofuranose (8a) (9.50 g, 38.9 mmol) was dissolved in acetic acid (60 mL). $H_2O$ (60 mL) was added and the resulting solution was stirred at ambient temperature overnight while monitoring by TLC for disappearance of starting material. The solution was concentrated on a rotary evaporator (~50° C.) to give 7.9 g (100%) of 3-deoxy-1,2-O-isopropylidene-α-D-glucofuranose (9a) as a viscous clear oil. This material was used in the next step without further purification: $^1$H NMR (400 MHz, $CDCl_3$) δ 5.72 (d, 1H), 4.67 (t, 1H), 4.11 (m, 1H), 3.78 (m, 1H+2OH), 3.75-3.79 (m, 1H), 3.44-3.49 (m, 1H), 1.97-2.02 (m, 1H), 1.74-1.81 (m, 1H), 1.44 (s, 3H), 1.25 (s, 3H).

Example 8

3-Deoxy-1,2-O-isopropylidene-α-D-xylofuranose (10a)

3-Deoxy-1,2-O-isopropylidene-α-D-glucofuranose (9a) was dissolved in $CH_3OH$ (50.0 mL), and $CH_2Cl_2$ (50.0 mL) was then added. $NaIO_4$ (10.0 g, 46.7 mmol) was added in one portion to this solution at ambient temperature. The resulting suspension was stirred at ambient temperature overnight, while monitoring by TLC for disappearance of starting material. The suspension was filtered, and the salts were then washed with $CH_2Cl_2$ (20 mL). The filtrate was transferred to a dry flask. $NaBH_4$ (4.0 g, 106 mmol) was slowly added in several portions to the combined stirring filtrate. After the suspension was stirred for 2 h at ambient temperature, TLC showed complete conversion from the intermediate aldehyde to 3-deoxy-1,2-O-isopropylidene-α-D-xylofuranose (10a). The solvent was removed on a rotary evaporator (~40° C.), and the residue was then partitioned between 10% aqueous NaCl (50 mL) and EtOAc (50 mL). The two phases were vigorously mixed, and then separated. The aqueous phase was extracted with EtOAc (3×50 mL). The combined organic extracts were washed with saturated aqueous NaCl (30 mL), dried over $Na_2SO_4$, and then filtered. The filtrate was concentrated on a rotary evaporator (~40° C.) to give 4.7 g (70%) of 3-deoxy-1,2-O-isopropylidene-α-D-xylofuranose (10a) as a white solid. $^1$H NMR (400 MHz, $CDCl_3$) δ 5.82 (d, 1H), 4.76 (t, 1H), 4.34-4.37 (m, 1H), 3.90 (dd, 1H), 3.56 (q, 1H), 1.99-2.04 (m, 1H), 1.82-1.89 (m, 1H), 1.76 (br s, 1H), 1.53 (s, 3H), 1.34 (s, 3H).

Example 9

3-Deoxy-1,2,5-tri-O-acetyl-α-D-xylofuranose (3B)

Aqueous $H_2SO_4$ (0.1 mL of a 1 M solution, 0.1 mmol) was slowly added to a solution of 3-deoxy-1,2-O-isopropylidene-α-D-xylofuranose (10a) (0.26 g, 1.5 mmol), glacial acetic acid (3 mL), and acetic anhydride (0.6 mL). The resulting solution was stirred at ambient temperature overnight and was then evaporated to dryness. The residue was partitioned between $H_2O$ and EtOAc. The phase mixture was shaken well and then separated. The aqueous phase was extracted with EtOAc. The combined organic fractions were dried over Na$_2$SO$_4$, filtered, and evaporated to dryness to provide crude 3-deoxy-1,2,5-tri-O-acetyl-α-D-xylofuranose (3B) as a mixture of α and β anomers. $^1$HNMR for the β anomer: (400 MHz, CDCl$_3$) δ 6.17 (s, 1H), 5.19 (d, 1H), 4.55-4.61 (m, 1H), 4.22 (d, 0.5; H), 4.20 (d, 0.5; H), 4.07-4.12 (m, 1H), 2.04-2.18 (m, 11H).

Example 10

3-Deoxy-1,2,5-tri-O-acetyl-α-D-xylofuranose (3B)

A solution of 3-deoxy-1,2-O-isopropylidene-α-D-xylofuranose (10a) (1.0 g, 5.7 mmol), CH$_2$Cl$_2$ (5 mL), acetic anhydride (2 mL), and pyridine (0.3 mL) was stirred at ambient temperature overnight. The solution was evaporated under vacuum to remove CH$_2$Cl$_2$. To the remaining solution at 0° C. was added acetic acid (18 mL), acetic anhydride (1 mL), and concentrated H$_2$SO$_4$ (1.2 mL) at). The resulting solution was warmed from 0° C. to ambient temperature and stirred for 24 h. The solution was cooled to 0° C. and 10% aqueous sodium acetate (150 mL) was added. The resulting solution was extracted with methyl t-butyl ether (MTBE) (2×100 mL). The combined MTBE extracts were sequentially washed with 5% aqueous NaHCO$_3$ (2×40 mL), water, and saturated aqueous NaCl (50 mL). The MTBE phase was evaporated to dryness to give 0.9 g of 3-deoxy-1,2,5-tri-O-acetyl-α-D-xylofuranose (3B) as a mixture of α and β anomers. $^1$H NMR analysis was the same as for that obtained from Example 9.

It is important to note that the construction and arrangement of the methods and steps shown in the exemplary embodiments is illustrative only. Although only a few embodiments of the present disclosure have been described in detail, those skilled in the art will readily appreciate that many modifications are possible without materially departing from the novel teachings and advantages of the subject matter recited in the claims. Accordingly, all such modifications are intended to be included within the scope of the present disclosure as defined in the appended claims. The order or sequence of any method or method steps may be varied or re-sequenced according to alternative embodiments. Other substitution, modification, changes and omissions may be made in the design, operating conditions and arrangement of the embodiments without departing from the spirit of the present disclosure as expressed in the appended claims.

All publications, patents and patent applications cited in this specification are herein incorporated by reference, and for any and all purposes, as if each individual publication, patent or patent application were specifically and individually indicates to be incorporated by reference. In this case of inconsistencies, the present disclosure will prevail.

The invention claimed is:

1. A method for the preparation of a compound of Formula (3)

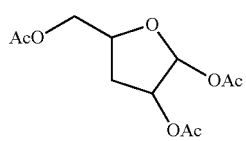

comprising:
(i) sulfonating a compound of Formula (6) with a sulfonating agent and a base

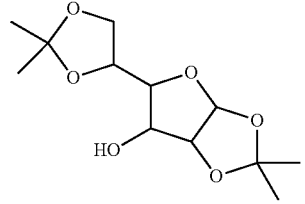

to form a sulfonyl substituted compound of Formula (7)

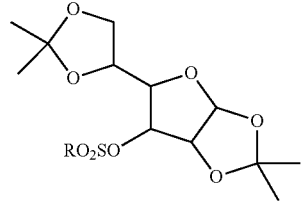

wherein R is an alkyl or aryl optionally substituted by 1-5 substituents selected from —OH, halo, —CN, C$_1$-C$_6$ alkyl, arylalkyl, C$_1$-C$_6$ alkoxy, C$_1$-C$_6$ alkenyl, C$_1$-C$_6$ hydroxyalkyl, amino, C$_1$-C$_6$ alkylamine, and C$_1$-C$_6$ dialkylamine, wherein the alkyl groups can be further substituted with one or more halogens;

(ii) reducing the sulfonyl substituted compound of Formula (7) with a reducing agent to form a compound of Formula (8)

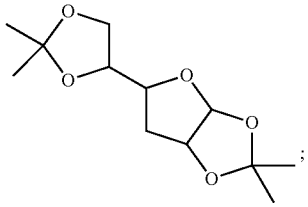

(iii) hydrolyzing the compound of Formula (8) with an acid to form a compound of Formula (9)

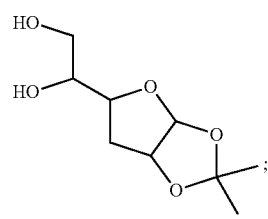

(iv) oxidizing the compound of Formula (9) with an oxidizing agent followed by reduction with a reducing agent to form a compound of Formula (10)

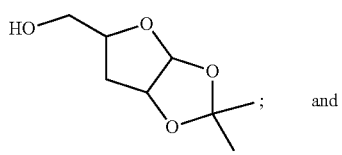

10

(v) acetylating the compound of Formula (10) with an acetylating agent in the presence of an acid catalyst to form the compound of Formula (3)

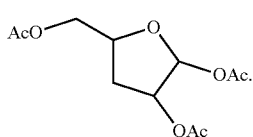

3

2. The method of claim 1 wherein the compound of Formula (3) has the orientation shown in Formula (3B)

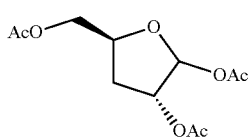

3B comprising:

(i) sulfonating a compound of Formula (6) having the orientation of Formula (6B), or Formula (6C), or mixtures thereof, with a sulfonating agent and a base

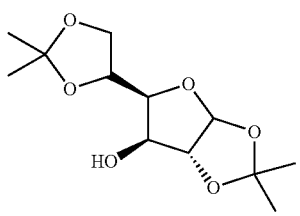

6B

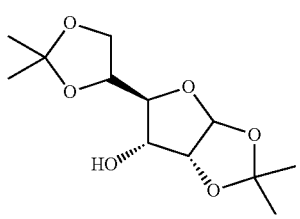

6C to form a sulfonyl substituted compound of Formula (7) having the orientation of Formula (7B), or Formula (7C), or mixtures thereof

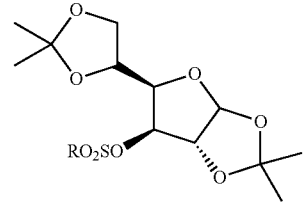

7B

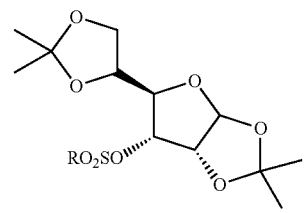

7C wherein R is an alkyl or aryl optionally substituted by 1-5 substituents selected from —OH, halo, —CN, $C_1$-$C_6$ alkyl, arylalkyl, $C_1$-$C_6$ alkoxy, $C_1$-$C_6$ alkenyl, $C_1$-$C_6$ hydroxyalkyl, amino, $C_1$-$C_6$ alkylamine, and $C_1$-$C_6$ dialkylamine, wherein the alkyl groups can be further substituted with one or more halogens;

(ii) reducing the sulfonyl substituted compound of Formula (7) having the orientation of Formula (7B), or Formula (7C), or mixtures thereof with a reducing agent to form a compound of Formula (8) having the orientation of Formula (8B)

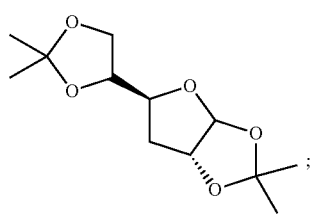

8B (iii) hydrolyzing the compound of Formula (8) having an orientation of Formula (8B) with an acid to form a compound of Formula (9) having an orientation of Formula (9B)

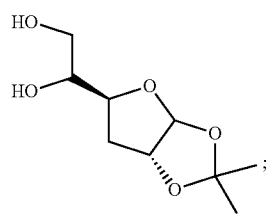

9B (iv) oxidizing the compound of Formula (9) having an orientation of Formula (9B) with an oxidizing agent followed by reduction with a reducing agent to form a compound of Formula (10) having an orientation of Formula (10B)

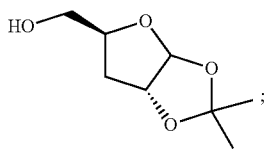

and (v) acetylating the compound of Formula (10) having the orientation of Formula (10B) with an acetylating agent in the presence of an acid catalyst to form the compound of Formula (3) having the orientation of Formula (3B)

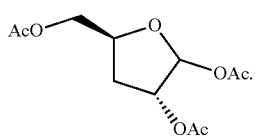

3. The method of claim 1 wherein the sulfonating agent is selected from the group consisting of an alkyl sulfonic anhydride, an alkyl sulfonic halide, an aromatic sulfonic anhydride, an aromatic sulfonic halide and mixtures thereof.

4. The method of claim 1 wherein the sulfonating agent is triflic anhydride.

5. The method of claim 1 wherein the reducing agent is a borohydride compound or an aluminum hydride compound.

6. The method of claim 1 wherein the oxidizing agent is selected from the group consisting of sodium periodate and lead acetate.

7. The method of claim 1 wherein R is $CF_3$, $CH_3$, or —$C_6H_4CH_3$.

8. The method of claim 1 wherein the base of reaction sequence (i) is at least one selected from the group consisting of pyridine, triethylamine, imidazole and diisopropylethylamine.

9. The method of claim 1 wherein an aromatic solvent is utilized in reaction sequence (ii).

10. The method of claim 1 wherein reaction sequence (iv) is conducted in a methanol solvent, a methylene chloride solvent, a methanol/methylene chloride solvent or a methanol/water solvent.

* * * * *